US012564514B2

(12) United States Patent
Teuma et al.

(10) Patent No.: US 12,564,514 B2
(45) Date of Patent: Mar. 3, 2026

(54) PATIENT INTERFACE DEVICE FOR LASER METHODS AND SYSTEMS

(71) Applicant: Lensar, Inc., Orlando, FL (US)

(72) Inventors: E. Valas Teuma, Orlando, FL (US);
John McWhirter, Winter Park, FL
(US); Michael Brownell, San
Clemente, CA (US)

(73) Assignee: Lensar, LLC., Orlando, FL (US)

( * ) Notice: Subject to any disclaimer, the term of this
patent is extended or adjusted under 35
U.S.C. 154(b) by 492 days.

(21) Appl. No.: 15/481,305

(22) Filed: Apr. 6, 2017

(65) Prior Publication Data

US 2017/0290703 A1 Oct. 12, 2017

Related U.S. Application Data

(60) Provisional application No. 62/319,728, filed on Apr.
7, 2016.

(51) Int. Cl.
| | |
|---|---|
| *A61F 9/008* | (2006.01) |
| *A61B 18/20* | (2006.01) |
| *A61F 9/009* | (2006.01) |

(52) U.S. Cl.
CPC .............. *A61F 9/008* (2013.01); *A61B 18/20*
(2013.01); *A61F 9/009* (2013.01); *A61F*
*2009/00865* (2013.01); *A61F 2009/0087*
(2013.01); *A61F 2009/00872* (2013.01); *A61F*
*2009/00887* (2013.01); *A61F 2009/00895*
(2013.01)

(58) Field of Classification Search
CPC ..................... A61F 9/008; A61F 9/009; A61F
2009/00865; A61F 2009/0087; A61F
2009/00872
See application file for complete search history.

(56) References Cited

U.S. PATENT DOCUMENTS

| | | | |
|---|---|---|---|
| 4,538,608 | A | 9/1985 | L'Esperance |
| 4,764,930 | A | 8/1988 | Bille |
| 4,901,718 | A | 2/1990 | Bille |
| 4,907,586 | A | 3/1990 | Bille |
| 5,098,426 | A | 3/1992 | Sklar |
| 5,246,435 | A | 9/1993 | Bille |
| 5,355,181 | A | 10/1994 | Ashizaki |

(Continued)

FOREIGN PATENT DOCUMENTS

| | | |
|---|---|---|
| EP | 1 350 492 | 10/2003 |
| WO | WO 98/031136 | 1/1998 |
| WO | WO 2005/011547 | 2/2005 |

OTHER PUBLICATIONS

Aug. 11, 2017. PCT, PCT/US17/26440 Search Report and opinion.
May 11, 2019, EPO, Exam Report Appl. No. 17779866.7.

*Primary Examiner* — Eric D. Bertram
(74) *Attorney, Agent, or Firm* — Belvis Law, LLC.; Glen
P. Belvis

(57) ABSTRACT
An optical interface device having an opening for an optical
path that can be non-circular and having engagement mem-
bers having gradually varying angles of engagement. An
embodiment of the interface device can be a one size fits all
device, providing a configuration that fits in all typical eye
openings, including narrow palpebral fissures and small
eyes, while providing optical path access to features and
structures of the eye. An embodiment of the interface device
engages the limbus, cornea and sclera.

35 Claims, 23 Drawing Sheets

(56) References Cited

U.S. PATENT DOCUMENTS

| | | | |
|---|---|---|---|
| 5,439,462 A | 8/1995 | Bille | |
| 5,480,396 A | 1/1996 | Simon | |
| 6,004,314 A | 12/1999 | Wei | |
| 6,099,522 A | 8/2000 | Knopp | |
| 6,197,018 B1 | 3/2001 | O'Donnell | |
| 6,312,422 B1 | 11/2001 | Dubnack | |
| 6,322,556 B1 | 11/2001 | Gwon | |
| 6,325,792 B1 | 12/2001 | Swinger | |
| 6,899,707 B2 * | 5/2005 | Scholler | A61F 9/009 |
| | | | 606/4 |
| 7,018,376 B2 * | 3/2006 | Webb | A61F 9/009 |
| | | | 606/4 |
| 7,655,002 B2 | 2/2010 | Myers | |
| 8,262,646 B2 | 9/2012 | Frey | |
| 8,382,745 B2 | 2/2013 | Naranjo-Tackman | |
| 8,394,084 B2 | 3/2013 | Palankar et al. | |
| 8,403,921 B2 | 3/2013 | Palankar et al. | |
| 8,425,497 B2 | 4/2013 | Blumenkranz et al. | |
| 8,465,478 B2 | 6/2013 | Frey | |
| 8,480,659 B2 | 7/2013 | Frey | |
| 8,500,723 B2 | 8/2013 | Frey | |
| 8,617,146 B2 | 12/2013 | Frey | |
| 8,652,131 B2 * | 2/2014 | Muller | A61F 9/0079 |
| | | | 606/41 |
| 8,758,332 B2 | 6/2014 | Frey | |
| 8,801,186 B2 | 8/2014 | Frey | |
| 9,180,051 B2 | 11/2015 | Frey | |
| 9,375,349 B2 | 6/2016 | Frey | |
| 9,545,338 B2 | 1/2017 | Frey | |
| 9,968,485 B2 | 5/2018 | McWhirter | |
| 2007/0173794 A1 | 7/2007 | Frey | |
| 2008/0287928 A1 | 11/2008 | Arnoldussen | |
| 2010/0004641 A1 | 1/2010 | Frey | |
| 2010/0274228 A1 * | 10/2010 | Mrochen | A61F 9/013 |
| | | | 604/541 |
| 2011/0022035 A1 * | 1/2011 | Porter | A61F 9/00825 |
| | | | 606/4 |
| 2011/0112519 A1 | 5/2011 | Donitzky | |
| 2011/0224657 A1 * | 9/2011 | Stevens | A61F 9/008 |
| | | | 606/5 |
| 2012/0016349 A1 * | 1/2012 | Brownell | A61F 9/009 |
| | | | 606/4 |
| 2012/0191077 A1 | 7/2012 | Mrochen | |
| 2014/0276673 A1 | 9/2014 | Heitel | |
| 2015/0088175 A1 * | 3/2015 | McWhirter | A61F 9/009 |
| | | | 606/166 |
| 2016/0302971 A1 | 10/2016 | Morely | |
| 2017/0239087 A1 * | 8/2017 | Sahler | A61F 9/009 |

* cited by examiner

ANTERIOR ⟷ POSTERIOR

ANTERIOR ⟷ POSTERIOR

PATIENT INTERFACE DEVICE FOR LASER METHODS AND SYSTEMS

This application claims under 35 U.S.C. § 119(e)(1) the benefit of the filing date of provisional application Ser. No. 62/319,728 filed Apr. 7, 2016, the entire disclosure of which is incorporated herein by reference.

BACKGROUND OF THE INVENTION

Field of the Invention

The present invention relates to devices and methods for interfacing an eye with systems for performing methods on and in the eye, including treating the structure of the cornea and the natural human crystalline lens to address a variety of medical conditions, such as presbyopia, refractive error, cataracts and combinations of these.

Embodiments of the present eye interfaces can be used with various interface devices, patient interface devices ("PIDs"), ophthalmic laser systems, ophthalmic treatment systems, ophthalmic measuring systems, ophthalmic diagnostic systems, and laser docking systems, examples of such devices and systems are disclosed and taught in US Patent Publication Nos. 2011/0022035, 2011/0190739, 2010/0022994, 2011/0187995, 2015/0088175 2007/0173794, 2007/0173794 and in U.S. Pat. Nos. 8,262,646, 9,180,051, 8,480,659, 8,708,491 8,382,745 and 8,801,186.

The anatomical structures of the eye are shown in general in FIGS. 11A, 11B, 11C. In FIG. 11A there is shown the front plan view and cross sectional view of the eye 150. The eye 150 has eyelids 151, an iris 102, a pupil 152, a cornea 101, a sclera 131. In FIG. 11B, which is a cross sectional view of the eye 150. The sclera 131 is the white tissue that surrounds the lens 103 except at the cornea 101. The cornea 101 is the transparent tissue that comprises the exterior surface of the eye through which light first enters the eye. The iris 102 is a colored, contractible membrane that controls the amount of light entering the eye by changing the size of the circular aperture at its center (the pupil 152). The ocular or natural crystalline lens 103, a more detailed picture of which is shown in FIGS. 11C, (utilizing similar reference numbers for similar structures) is located just posterior to the iris 102. The terms ocular lens, natural crystalline lens, natural lens, natural human crystalline lens, and lens (when referring to the prior terms) are used interchangeably herein and refer to the same anatomical structure of the human eye.

Generally, the ocular lens changes shape through the action of the ciliary muscle 108 to allow for focusing of a visual image. A neural feedback mechanism from the brain allows the ciliary muscle 108, acting through the attachment of the zonules 111, to change the shape of the ocular lens. Generally, sight occurs when light enters the eye through the cornea 101 and pupil 152, then proceeds through the ocular lens 103 through the vitreous 110 along the visual axis 104, strikes the retina 105 at the back of the eye, forming an image at the macula 106, having a fovea 154, that is transferred by the optic nerve 107 to the brain. The interior of the eye 150 has a choroid 155. The space between the cornea 101 and the retina 105 is filled with a liquid called the aqueous 117 in the anterior chamber 109 and the vitreous 110, a gel-like clear substance, in the chamber posterior to the lens 103.

Generally when viewing the eye relative to the face, and as shown in FIG. 11A, there is a vertical axis 180 and a horizontal axis 181, which is also know as the nasal-temporal axis.

FIG. 11C illustrates, in general, components of and related to the lens 103 for a typical 50-year old individual. The lens 103 is a multi-structural system. The lens 103 structure includes a cortex 113, and a nucleus 129, and a lens capsule 114. The capsule 114 is an outer membrane that envelopes the other interior structures of the lens. The lens epithelium 123 forms at the lens equatorial 121 generating ribbon-like cells or fibrils that grow anteriorly and posteriorly around the ocular lens. The nucleus 129 is formed from successive additions of the cortex 113 to the nuclear regions. The continuum of layers in the lens, including the nucleus 129, can be characterized into several layers, nuclei or nuclear regions. These layers include an embryonic nucleus 122, a fetal nucleus 130, both of which develop in the womb, an infantile nucleus 124, which develops from birth through four years for an average of about three years, an adolescent nucleus 126, which develops from about four years until puberty which averages about 12 years, and the adult nucleus 128, which develops at about 18 years and beyond.

The embryonic nucleus 122 is about 0.5 mm in equatorial diameter (width) and 0.425 mm in Anterior-Posterior axis 104 (AP axis) diameter (thickness). The fetal nucleus 130 is about 6.0 mm in equatorial diameter and 3.0 mm in AP axis 104 diameter. The infantile nucleus 124 is about 7.2 mm in equatorial diameter and 3.6 mm in AP axis 104 diameter. The adolescent nucleus 126 is about 9.0 mm in equatorial diameter and 4.5 mm in AP axis 104 diameter. The adult nucleus 128 at about age 36 is about 9.6 mm in equatorial diameter and 4.8 mm in AP axis 104 diameter. These are all average values for a typical adult human lens approximately age 50 in the accommodated state, ex vivo. Thus this lens (nucleus and cortex) is about 9.8 mm in equatorial diameter and 4.9 mm in AP axis 104 diameter. Thus, the structure of the lens is layered or nested, with the oldest layers and oldest cells towards the center.

The lens is a biconvex shape as shown in FIGS. 11A, 11B and 11C.

The anterior and posterior sides of the lens have different curvatures and the cortex and the different nuclei in general follow those curvatures. Thus, the lens can be viewed as essentially a stratified structure that is asymmetrical along the equatorial axis and consisting of long crescent fiber cells arranged end to end to form essentially concentric or nested shells. The ends of these cells align to form suture lines in the central and paracentral areas both anteriorly and posteriorly. The older tissue in both the cortex and nucleus has reduced cellular function, having lost their cell nuclei and other organelles several months after cell formation.

As used herein, unless stated otherwise, generally, the term "about" is meant to encompass a variance or range of ±10%, the experimental or instrument error associated with obtaining the stated value, and preferably the larger of these.

In general, presbyopia is the loss of accommodative amplitude. In general, refractive error is typically due to variations in the axial length of the eye. Myopia is when the eye is too long resulting in the focus falling in front of the retina. Hyperopia is when the eye is too short resulting in the focus falling behind the retina. In generally, cataracts are areas of opacification of the ocular lens which are sufficient to interfere with vision. Other conditions, for which the present invention is directed, include but are not limited to the opacification of the ocular lens and astigmatism.

SUMMARY

There has existed a long standing need for improved apparatus and methods of interfacing optical and ophthalmic, analysis, treatment, therapeutic systems and devices with the human eye. These needs include the long standing need to fit, and preferably fit comfortably in various shapes and sizes of eyes, securely and safely affix to the surface of an eye, and to provide enhanced field of view to therapeutic, measuring, and other laser beam paths, to the structures of the eye. As laser measuring, therapeutic, and analysis ophthalmic systems increase in their capability's these needs for improved interface devices will likely increase, and become more important. The present inventions, among other things, solve these and other needs by providing the articles of manufacture, devices and processes set forth in this specification, drawings and claims.

Thus, there is provided a method of attaching an interface device to a surface of a human eye, the method including: bringing a first flexible contact member into contact with the surface of the human eye; bringing a second flexible contact member into contact with the surface of the human eye; wherein, the first contact member and the second contact member define a zone, the zone defining an area on the surface of the eye; reducing the pressure in the zone, thereby creating a reduced pressure zone and an area of reduced pressure on the surface of the eye; wherein the area of reduced pressure is in the shape of a non-planar ellipse.

There are further provided these methods, systems and devices that have one or more of the following features: wherein the first flexible contact member is an inner contact member and defines a contact member angle of greater than 90°; wherein the second contact member defines a contact member angle of less than 90°; wherein a portion of the first flexible contact member touches the eye first; wherein a portion of the second flexible contact member touches the eye first; wherein the contact member angle is about 120°; and, wherein the second contact member contact member is about 50°.

Additionally, there is provided a method of delivering a laser beam to an eye, the method including: attaching an interface device to a surface of a human eye; the interface device defining an opening, and having an inner contact member and an outer contact member, the method of attaching the interface device including: bringing the inner contact member into contact with the surface of the human eye; bringing the outer contact member into contact with the surface of the human eye; wherein, the inner contact member and the outer contact member define a zone, the zone defining an area on the surface of the eye, the area on the surface of the eye adjacent to the peripheral of the opening; reducing the pressure in the zone, thereby creating a reduced pressure zone and an area of reduced pressure on the surface of the eye; wherein the area of reduced pressure is in the shape of a non-planar ellipse; and, delivering a laser beam through the opening and into the eye.

There is further provided these methods, system and devices having one or more of the following features: wherein the open has a curved window, and having delivering the laser beam through the curved window and into the eye; wherein the curved window contacts the surface of the eye and changes the shape of the eye; wherein the open has a planar applanation window, and having delivering the laser beam through the planar applanation window and into the eye; wherein the opening defines a major and a minor axis; and the first member contacts a sclera of the eye, and does not contact a limbus of the eye along the major axis; wherein the inner member contacts the sclera at the major axes and does not contact the limbus; wherein the inner member contacts the limbus at the minor axis; and, wherein the opening is larger than the iris, and thereby the device does not obstruct the iris; and wherein the major axis of the opening at the distal end of the device is from about 1.01 to about 1.25 times larger than the minor axis at the opening at the distal end of the device.

An interface device for fixing on a human eye and operably connecting to an ophthalmic therapeutic, monitoring, diagnostic, or evaluative device, the interface device having: a body having an upper and a lower section, wherein the lower section defines a distal end of the interface device for contacting a surface of the eye and the upper section defines a proximal end of the interface device; whereby the proximal and distal ends define a device height along a vertical axis of the device; the lower section of the body defining an outer shape; the upper and lower sections of the body defining an opening through the device; the device having a major and a minor axis, wherein when in use the major axis corresponds to a nasal temporal axis; the lower section having an inner and an outer contact member; the contact members each having a distal end; wherein the distal ends of the contact members form the distal end of the device; the inner connect member having a height, and the outer contact member having a height; and, wherein the height of the outer contact member, the height of the inner contact member or both, varies between a point intersecting the major axis and a point intersecting the minor axis.

Still further there is provided these methods, systems and devices having one or more of the following features: wherein the major axis of the opening at the distal end of the device is from about 1.1 to about 1.2 times larger than the minor axis; wherein the major axis of the opening at the distal end of the device is from about 1.15 to about 1.19 times larger than the minor axis; wherein the major axis of the opening at the distal end of the device is from about 1.01 to about 1.21 times larger than the minor axis; wherein the distal end of the inner contact member is shorter at the minor axis and taller at the major axis; wherein the distal end of the outer contact member is shorter at the minor axis and taller at the major axis; wherein the distal end of the inner contact member defines a shape of a non-planar ellipse; wherein the distal end of the outer contact member defines a shape of a non-planar ellipse; wherein the distal end of the inner contact member and the distal end of the outer contact member define a shape of a non-planar ellipse; wherein the inner contact member defines a contact member angle of greater than 90°; and, wherein the outer contact member defines a contact member angle of less than 90°.

Still additionally, there is provided an interface device for fixing on a human eye and operably connecting to an ophthalmic therapeutic, monitoring, diagnostic, or evaluative device, the interface device having: a body having an upper and a lower section, wherein the lower section defines a distal end of the interface device for contacting a surface of the eye and the upper section defines a proximal end of the interface device; whereby the proximal and distal ends define a device height along a vertical axis of the device; the lower section of the body having a ridged annular channel; the ridged annular channel containing and holding a flexible insert; the flexible insert having an inner contact member and an outer contact member; and forming a flexible annular zone for maintaining a reduced pressure when engaged with a surface of the eye; the upper and lower sections of the body defining an opening through the device; the device having a major and a minor axis, wherein when in use the major axis corresponds to a nasal temporal axis; and, wherein the major axis of the opening at the distal end of the device is from about 1.03 to about 1.1 times larger than the minor axis.

DESCRIPTION OF THE PREFERRED EMBODIMENTS

Figure 1:
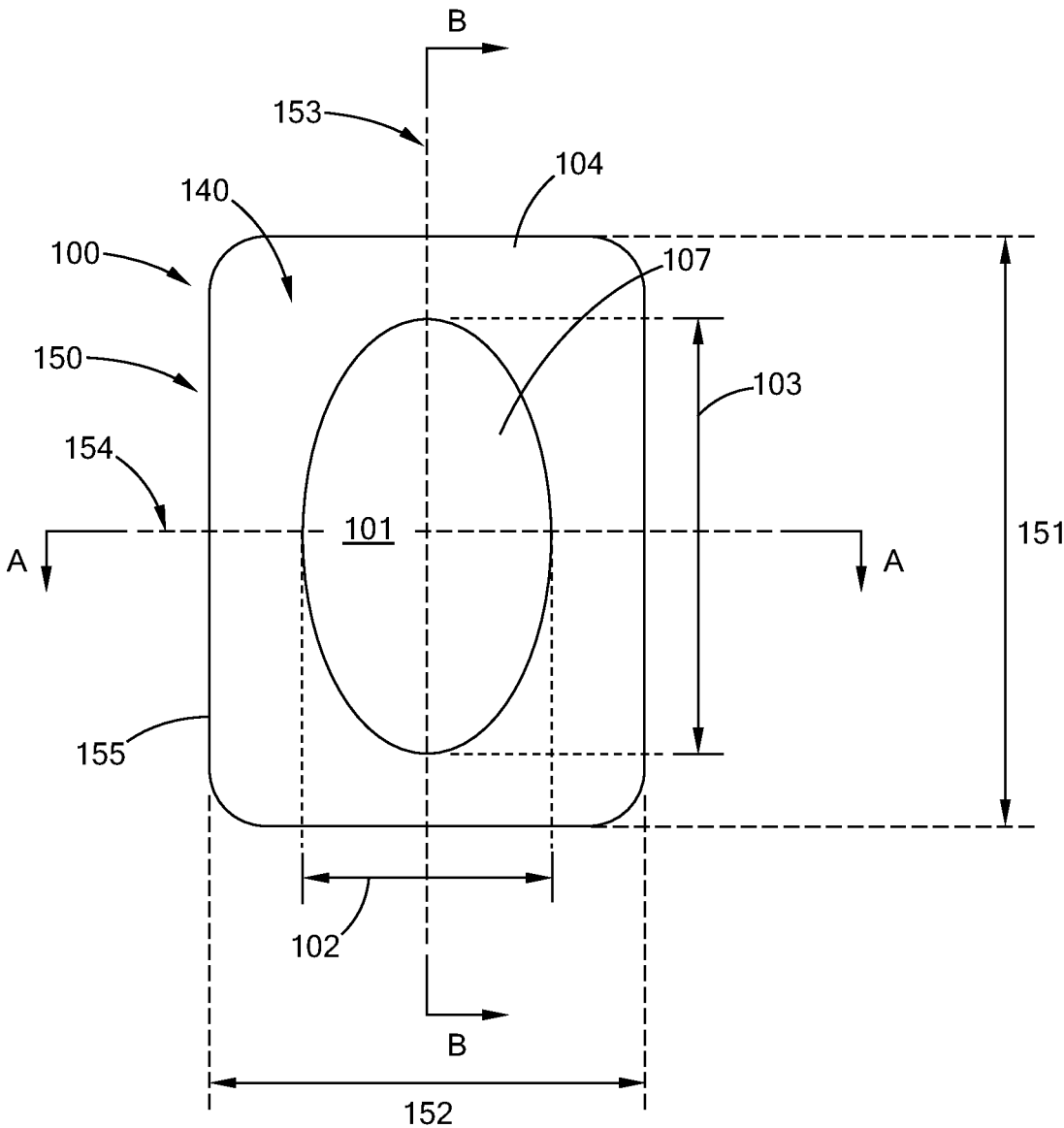
FIGS. 1 is a planar view of the top (proximal) side of an interface device in accordance with the present inventions.

The present invention relates to devices and methods for interfacing an eye with systems for performing methods on and in the eye, including addressing conditions, diseases, and other states of the eye, including the various structures of the eye. In embodiments of the interface devices the associated laser system can perform methods on the structure of the cornea, the natural human crystalline lens, and both, for diagnostic procedures, for monitoring and analysis procedures, and to address a variety of conditions of the eye, such as presbyopia, refractive error, astigmatism, induced astigmatism, cataract retardation, cataracts, and combinations of these and other conditions.

Embodiments of the present inventions provide, among other things, improved devices and methods of interfacing optical and ophthalmic, analysis, treatment, therapeutic systems and combinations and variations of such devices with eyes, and in particular with the human eye. These embodiments, among other things, fit, and preferably fit comfortably, in various shapes and sizes of eyes, and in a preferred embodiment a single interface device can fit in the vast majority of human eyes. Embodiments further can securely and safely affix to the surface of an eye. Embodiments include eye interfaces, e.g., eye cups and eye pieces, that are designed for small eyes and narrow palpebral fissures (eyelid aperture), preferably embodiments of these eye interface devices can be used in most, the vast majority (e.g., 95%) and all normal eye openings, e.g., palpebral fissures, of typical adults across all ethnicities. These eye interface assemblies are used with, or can be a part of, a PID, and as a part of an ophthalmic system, e.g., therapeutic system, monitoring system, diagnostic system, etc. While fitting in many eye shapes, and affixing to the surface of the eye, embodiments of the present inventions can provide enhanced field of view for therapeutic, measuring, and other imaging or diagnostics tools or devices, including laser beam paths, to the structures of the eye, e.g., cornea, limbus, sclera, and lens.

Although this specification focuses on applications to, and embodiments for use with human eyes, it should be understood that the present inventions are not so limited and embodiments of the present inventions can have equine, canine, and other veterinarian applications.

Embodiments of the present inventions can find applications, and utilization to enhance, augment and improve prior and existing laser ophthalmic systems, including the systems disclosed and taught in U.S. Patent Publication Nos. 2011/0022035, 2011/0190739, 2010/0022994, 2011/0187995, 2015/0088175 2007/0173794, 2007/0173794 and in U.S. Pat. Nos. 8,262,646, 9,180,051, 8,480,659, 8,708,491 8,382, 745 and 8,801,186, the entire disclosure of each of which is incorporated herein by reference. Such applications and utilization can include existing and prior commercially available systems, such as CATALYS laser systems, INTRALASE laser systems, VISX laser systems, WAVE-LIGHT laser systems, LENSX laser systems, as well as, other laser ophthalmic systems, e.g., Excimer, femtosecond and others. Embodiments, of the present inventions, can also finding application in, as well as lead to, the development of improved ophthalmic laser systems and methods.

In general, an embodiment of the present interface device has a housing that forms an inner opening and an outer boundary. The housing can be made from a single integral piece, structure or member, or it can be made from several components that are affixed together (either integrally or removably). The housing supports, or has as a part of it, a mechanism for engaging against the surface of the eye, e.g., the epithelium, the limbus, the cornea, the sclera and combinations and variations of these. This engagement mechanism can have, or be associated with, or the housing can otherwise have or form, a suction mechanism for attaching or affixing the interface device to the surface of the eye.

The housing forms, or has an inner opening and an outer shape defined by an outer surface. Typically the inner opening forms a passage that in some embodiments can provide, one or more of the following features, among other things, a passage for the therapeutic laser beam and beam path, a passage for an illumination light source (e.g., structure location and position determining laser beam or light source, or sources) and light path, an analysis light source, access to provide medicaments or treatments to the eye, a fluid holding chamber, a window (e.g., a contact lens to match the shape of the eye, a flat application lens, and a curved application lens to force the surface of the eye into the curved shape of the lens), and potentially access for tools to the eye.

In general, in an embodiment, the inner opening can have many different shapes, when viewed in two-dimensions from a top planer view, e.g., circular, elliptical, rectangular, square, rectangles having radiuses on their corners, and other shapes having multiple curves, arcs, angles and straight edges, and combinations and various of these. The inner opening shape when viewed in three-dimensions has a distal end or side (which is adjacent or closest to the surface of the eye) and a proximal end or side which is closes to the laser beam source. The inner opening can have a distance between the proximal and distal ends defining a depth or height. The distal and proximal ends can be the same shape, or they can have different shapes. The proximal end can be plainer, curved, and also have have engagement mechanisms (e.g., keys, latches, clips, threads) for engaging to the laser system or other device. The distal end can be plainer, curved, and combinations and variations of this. In an embodiment the distal end of the inner opening can be any non-circular shape that is projected on a spheroid. Preferably, the shape is that of an ellipse project on a spheroid. In embodiments, the shape of the spheroid is a shape that is similar to the shape of the anterior portions of the eye.

Figure 16A:
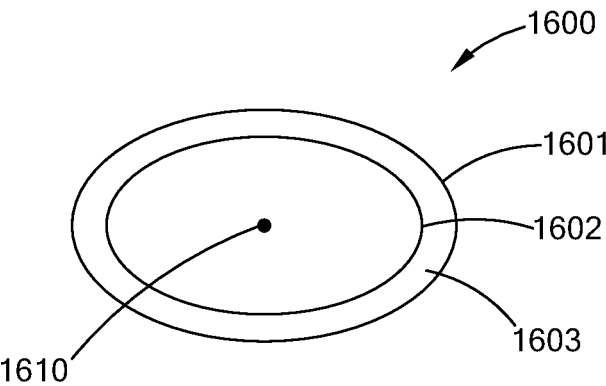
FIG. 16A is a bottom plan view of a non-planar ellipse shaped reduced pressure zone in accordance with the present inventions.
Figure 16B:
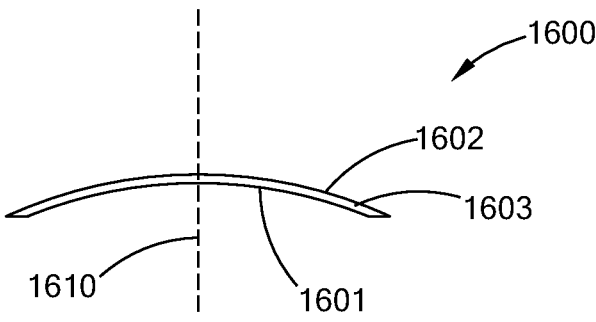
FIG. 16B is a side plan view of the non-planar ellipse shaped reduced pressure zone of FIG. 16A.

Thus, in a preferred embodiment the distal end of the inner opening, which can be, or includes, the distal end of the inner contact member, is in the shape of an ellipse projected on a sphere, which results in a non-planar elliptical shape. Similarly, the distal end of the inner opening, which can be, or includes, the outer contact member is in the shape of an ellipse projected on a sphere. In this manner, upon engagement with the eye, the inner and outer contact members form a zone of reduced pressure, which on the surface of the eye, is in the shape of an ellipse projected on a sphere, which results in the reduced pressure area on the eye being in the shape of a non-planar ellipse. Turning to FIGS. 16A and 16B, an embodiment of this configuration and reduced pressure zone and surface area are illustrated. Thus, FIG. 16A is a bottom plan view of a non-planar ellipse shape 1600 and FIG. 16B is a side plan view of the non-planar ellipse shape 1600. For reference, the view of FIGS. 16A and 16B are shown with respect to the vertical axis 1610. In this embodiment, the bottom or distal end of the inner contact member has the shape 1602 and the bottom or distal end of the outer contact member has shape 1601 form a vacuum zone having the shape 1603, which shapes are non-planar ellipses.

The housing similarly has a distal and proximal end or side, which can be coincident with, or form some or all of, the distal and proximal ends of the inner opening, respectively. Preferably, the engagement mechanism can be located on, and more preferably integral with, the proximal end of the housing.

In a preferred embodiment, the outer shape of the housing, which in general can be formed by the outer surface of the housing, is generally in the shape of an elliptic cylinder. The elliptic cylinder has a major (i.e., longer) and minor (i.e. shorter) axis. When placed on the eye, the major axis is generally aligned with the nasal-temporal axis of the eye, and the minor axis is generally aligned with the vertical axis of the eye.

In an embodiment of the interface devices, the distal end of the housing, the inner opening, or both, have contact members (e.g., flaps, panels, ridges, skirts, lips, etc.) that directly contact the surface of the eye and which form a seal against to eye to provide for, assist in forming, a reduced pressure zone, e.g. a vacuum, to hold the housing, and thus the interface device, to the eye. The members can form different angles with the distal end of the housing, thus providing for a varying contact member angle. The contact member angle can, for example, be at about 0° (parallel with the vertical axis of the housing or body), up to about 15° to about 15° (on either side of vertical, e.g. pointing inward and pointing out ward), up to about 30° to about 30°, up to about 90° to about 90° (i.e. flush with the housing end). The contact member angle does not need to be the same around the entirety of the opening, or along the entirety of the contact member. Thus, the angle can change as one moves a long or around the contact member. For example, in a device having a major and minor axis the contact member angle can vary from about 5° at the major axis points and about 35° at the minor axis points, to about about 35° at the major axis points and about 15° at the minor axis points. (Typically, each axis intersects the contact member at two points, i.e., the axis points.) The variation can be form 0-90° at two, three, four, five, six and more points along the contact member.

Preferably, these transitions of the angle are gradual, and in particular, the transition of the angle from major to minor axis and back again is gradual. It also being understood that the angle can vary in others manners with respect to the major and minor axis (e.g., the angle is the same at all axis points and varies in the area between the axis points, the angle is different at each axis point, and other combinations and variations of these). Further the contact member having a varying angle can be utilized in other embodiments not having a major and minor axis.

Turning to FIG. 1 there is shown a plan view of the top or proximal end 140 of an embodiment of an interface device 100 of the present inventions. The interface device 100 has an opening 101 in a body 104 (e.g., housing or structure). The body 104 has an outer shape 150, which is formed by outer surface 155. The outer shape has a length 151, which corresponds to a major axis 153, and a width 152, which corresponds to a minor axis 154. In general the outer shape is rectangular with radiused corners.

The body 104 can be made from injection molded plastics, plastics, polymers, metals, ceramics, glass, composites, other materials, and combinations and variations of these. The body 104 can be a single integral piece or can have several components that are glued, welded or otherwise affixed to each other. The body 104 can be disposable, so that it is single use, for a single patient only, or it can be reusable (e.g., capable of withstanding sterilization and cleaning procedures).

In general the outer shape 150 of the housing, and in this embodiment of the device itself, since the housing outer shape of the housing and outer shape of the device are the same, should be of a size that permits it to fit in the opening for the eye in the face and fit between the eye lids. Thus, the outer diameter of the lower portion of the device, i.e., the distal end, for the major axis should be about 19 mm, about 20 mm, about 21 mm, and from about 17 to about 22 mm, and about 19 to about 21 mm, slightly larger and smaller sizes are also contemplated. Thus, the outer diameter of the lower portion of the device, i.e., the distal end, for the minor axis should be about 16 mm, about 17 mm, about 18 mm, about 19 mm, and from about 17 mm to about 19 mm, and about 18 mm to about 19 mm, slightly larger and smaller sizes are also contemplated The interface device 100 has an inner opening 101 that is formed by, or in, the body 104. The inner opening 101 has a length 103 that corresponds to the major axis 153 and a width 102 that corresponds to the minor axis 154.

Figure 1A:
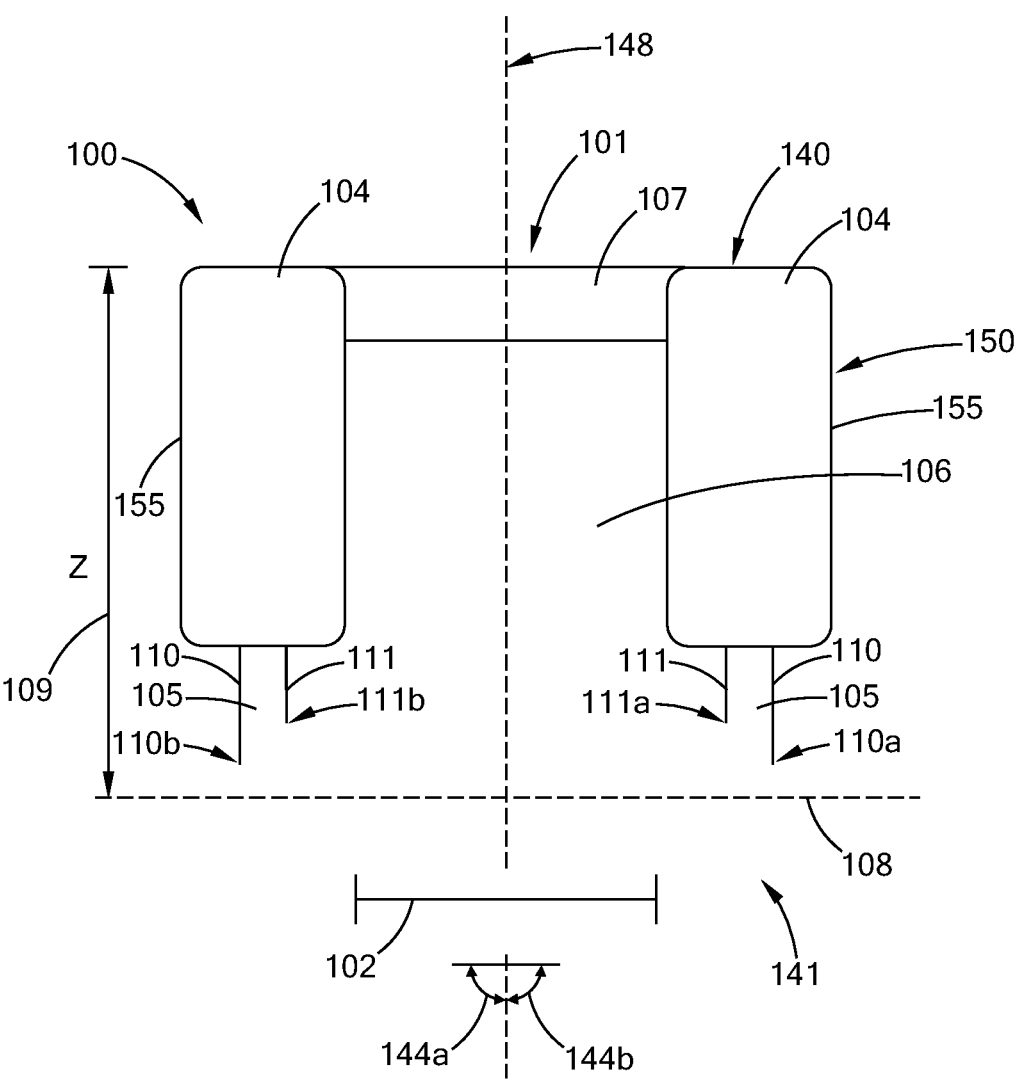
FIG. 1A is a cross sectional view of the device of FIG. 1 along line A-A.
Figure 1B:
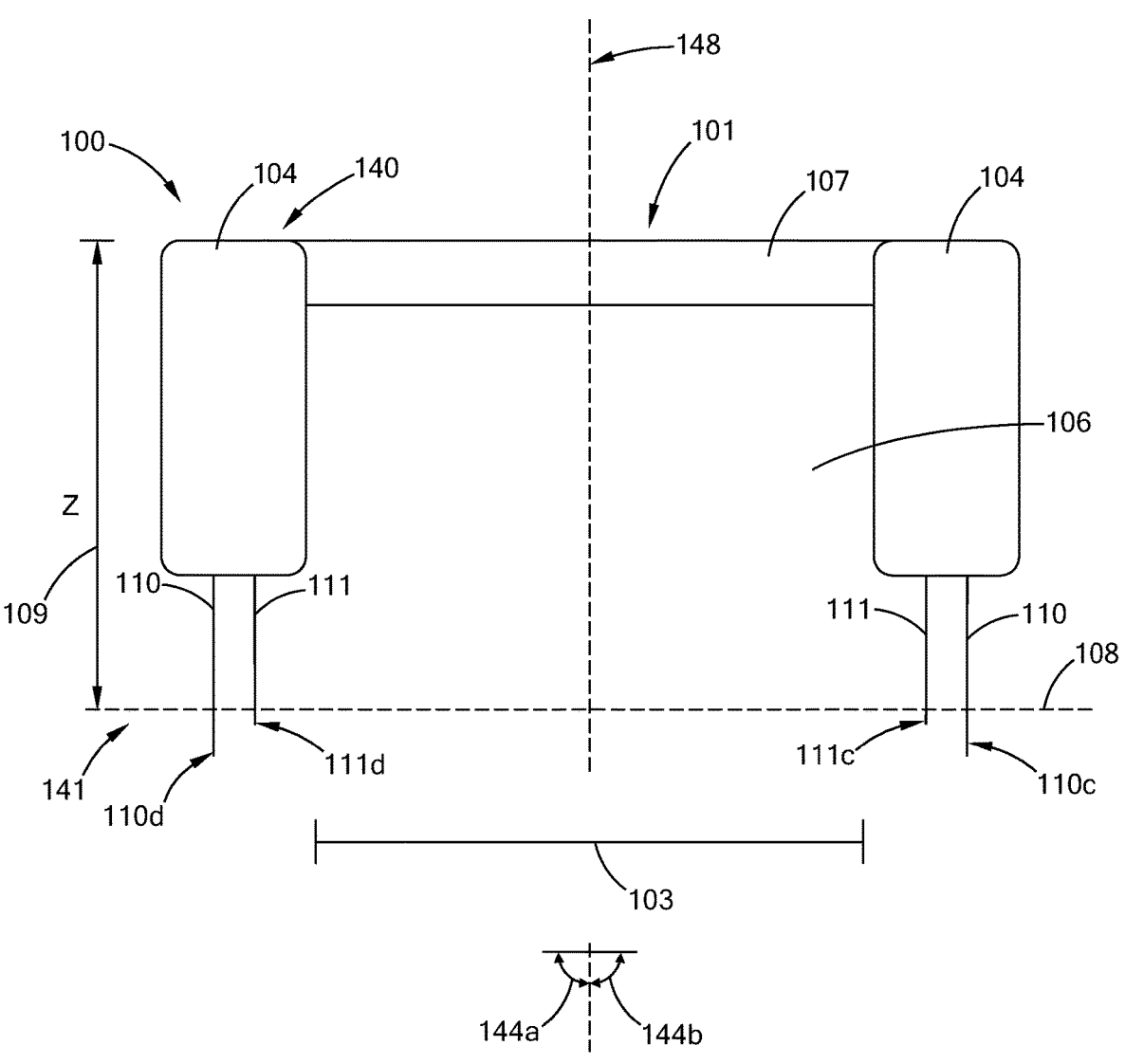
FIG. 1B is a cross sectional view of the device of FIG. 1 along line B-B.

Continuing with FIG. 1, while turning to FIGS. 1A and 1B, which are cross sectional views of the device 100 taken along lines A-A, and B-B respectively, further structures of the embodiment of the device 100 are shown. Thus, FIG. 1A is a cross sectional view along the minor axis 154, and FIG. 1B is a cross sectional view along the major axis 153.

The inner opening 101 has a cover plate 107. The cover plate 107 in this embodiment is a planer window, that is transmissive to the laser beam wavelength. It being understood that in some embodiments no cover plate is used, the cover plate can be a contact lens, the cover plate can be an applicator, the cover plate can be curved, e.g., generally following the shape of the cornea, or curved in a predetermined shape that forces the cornea to conform with the cover plate. Further the cover plate can be positioned along the height 109 (z direction 109 can be referred to as the height or depth of the device and opening), such that the cover plate does not touch the surface of the eye, only partially touches the surface of the eye, touches the surface of the eye to the extent that the eye is applanated, e.g., flattened or forced to a different curvature or shape.

In the embodiment of FIGS. 1, 1A & 1B, the cover plate or window 107 is located at the proximal end 140 of the device body 104. At the distal end of the body 104 there are located an inner sealing member 111 and an outer sealing member 110. In this embodiment both engagement members, e.g., the sealing members 111, 110, have an angel, e.g., the contact member angle, of 0° to the vertical access 148 of the body (the height of the body is determined along this axis and is the distance from the proximal end of the device to the distal end). The sealing members would each be contact members.

It being understood that in embodiments the contact member can be biased or angled inward, i.e. into or towards the opening 101, as shown by arced arrow 144a or outwardly, i.e., away from the opening 101, as shown by arced arrow 144b. These angles 144a, 144b, in various embodiments can be from 0° to 90°.

The inner 111 and outer 110 sealing members engage the surface of the eye (not shown) and seal against that surface, forming an annular reduce pressure zone 105. The pressure in zone 105 can be reduced by having the zone connected via channels or tubes (not shown in the figure) to a vacuum pump or similar device.

The pressure can be a sufficient pressure that does not damage the eye. The pressure can be lower during initial contact (i.e., more suction) as the device is affixed to the eye, and then can be increased, (i.e., the amount of suction is reduced) during the procedure to reduce stresses on the eye, yet still prevent, reduce or minimize, the device from breaking away or otherwise becoming dislodged from the surface of the eye. Upon completion of the procedure, or for any other reason to remove the device, the reduced pressure is broken and the zone 105 is returned to ambient pressure, or a slight positive pressure to assist with the removal of the device from the surface of the eye.

The inner sealing member 111 further forms a sealing zone 106. This sealing zone 106 can be at ambient pressure, can hold a fluid (e.g. saline), can have air, a humidified gas, can have a reduced pressure, can have an increased pressure, and combinations and variations of these.

The device 100 as shown in FIGS. 1, 1A & 1B is in an unengaged state, i.e., the device has not yet been engaged with the surface of the eye. Upon engagement the inner and outer sealing members 111, 110 can deform so to increase the amount of contact (e.g. contact surface area) they have with the surface of the eye. The surface of the sealing member that engages, e.g., contacts the surface of the eye can also have ribs, channels, and other surface features to enhance the forming of a seal against the surface of the eye.

In the unengaged (and preferably the engaged) state of the device 100, the outer engagement member 110 has distal ends 110a, 110b, 110c, 110d, and the inner engagement member 111 has distal ends 111a, 111b, 111c, 111d. In the embodiment of FIGS. 1, 1A & 1B, the inner member 111 is shorter than the outer member 110. Further, as seen in FIG. 1A, the inner member ends 111a, 111b, which ends intersect the plane of the minor axis 154, are the same distance from the bottom of the body 104, and are the same distance above an imaginary plane 108, which is a distance "Z" from the top of the body 104 as shown by arrow 109. Similarly, the outer member ends 110a, 110b, which ends intersect the plane of the minor axis 154, are the same distance from the bottom of the body 104, and are the same distance above an imaginary plane 108, which is a distance "Z" from the top of the body 104 as shown by arrow 109. The outer member ends 110a, 110b are closer to the imaginary plane 108, than are the inner member ends 111a, 111b.

Turning now primarily to FIG. 1B, which is a cross sectional view along the major axis 153, the inner and out members 111, 110 are longer at the location where they intersect the major axis 153, than they are at the location where they intersect the minor axis 154. Thus, the inner member ends 111c, 111d, which ends intersect the plane of the major axis 153, are the same length, and are below the imaginary plane 108. Similarly, the outer member ends 110c, 110d, which ends intersect the plane of the major axis 153, are the same length, and are below the imaginary plane 108. Thus, as shown in FIGS. 1A and 1B as one moves around the contact member (formed by inner and outer sealing members 111, 110) the length of the contact member increases and decreases as the member crosses the major and minor axes.

It being understood that in embodiments the inner member can be longer at the minor axis and shorter at the minor axis, the outer member can be longer at the minor axis and short at the major axis and combinations and variation of these.

Figures 2A, 2B:
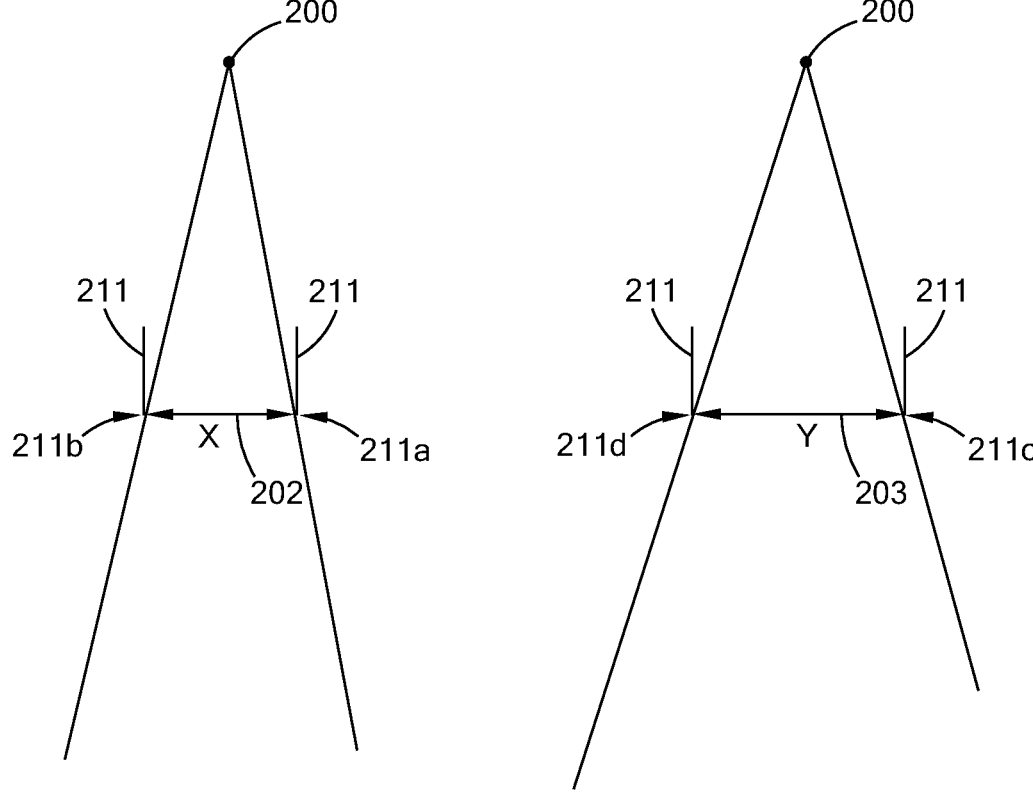
FIG. 2A is a cross sectional view of an image media path along the short axis of the opening of an embodiment of a device in accordance with the present inventions.
FIG. 2B is a cross sectional view of an image media path along the long axis of the opening of an embodiment of a device in accordance with the present inventions.

Turning to FIGS. 2A and 2B, there are shown cross sectional views of the imaging media, media path, which could also be the therapeutic media, media path and a diagnostic media, media path. The imaging media can be light, non-coherent light, acoustic, e.g., ultrasound, coherent light, e.g., a laser beam, a plurality of light sources, and other medical imaging media. If the imaging media is a light source the path will be referred to as an optical imaging path. FIG. 2A is a cross sectional view of the imaging path 200 along the shorter, e.g., minor, axis, and the path 200 has a distance "X" 202 between the ends 211a, 211b of the inner sealing member 211. FIG. 2B is a cross sectional of the imaging path 200 along the longer, e.g. major axis and the path 200 has a distance "Y" 203 between the ends 211*c*, 211*d* of the inner sealing member 211. In embodiments, the distance Y is greater than the distance X. Thus, in embodiments, the distance Y can be about 1.01× larger, about 1.03× larger, about 1.05× larger, about 1.08× larger, about 1.1× larger, about 1.15× larger, about 1.18× larger, about 1.2× larger, about 1.25× larger, from about 1.01× to about 1.3× larger, from about 1.03× to about 1.2× larger, from about 1.04× to about 1.1× larger, and from about 1.5× to about 1.8× larger, as well as other multiples.

Similar multiples for the major and minor axis dimensions of the outer diameter of the distal end of the device are utilized.

Thus, it can be seen that the dimensions of the major and minor axes of the inner sealing members, as well as the opening, when selected in conjunction with the major and minor axis of the outer surface of the house can provide an optimal, e.g., large, larger, largest, imaging media path for an interface device that can fit into the optimal, e.g., essentially all, the vast majority, and all typical, eye opening shapes and sizes. Thus, this optimization of housing outer shapes and sizes with inner opening shape and sizes gives embodiments of the present inventions to be essentially a one size fits all interface device.

These imaging media path optimizations are also possible for the laser beam path, which could be essentially the same as, and in some embodiments the same as the imaging media path. (It being understood that the pupil, which is not shown in FIGS. 2A and 2B, can effect and in embodiments limit the size of the media path.)

Figure 3:
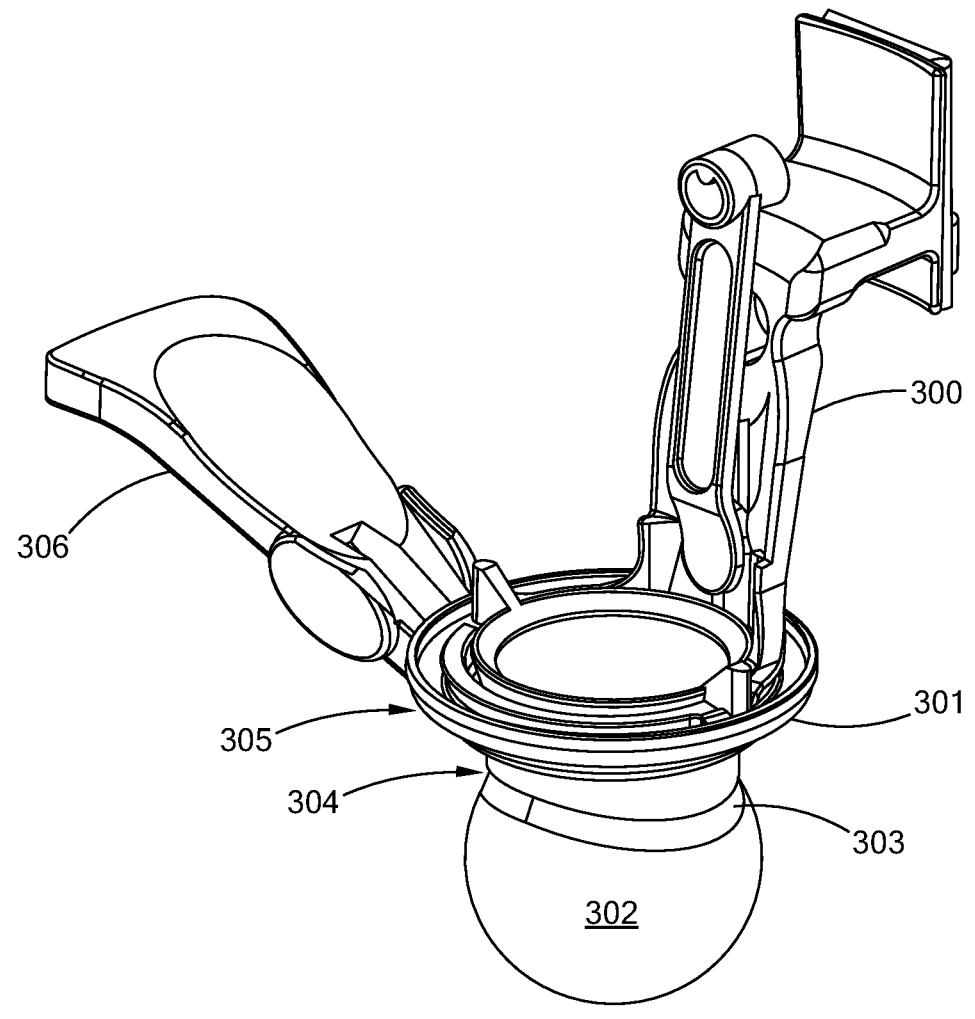
FIG. 3 is a perspective view of an embodiment of an interface device in accordance with the present inventions.

Turning to FIG. 3 there is shown a perspective view of an embodiment of a laser interface device 301 attached to an engagement arm 300 for engaging the interface device 301 with a laser system (not shown). Engagement arm 300, laser systems, and other apparatus and procedures for interfacing the laser, laser path, and laser systems with an interface device and the eye are disclosed and taught in U.S. Patent Application Publication No. 2015/0088175, the entire disclosure of which is incorporated herein by reference.

The interface device 301 is attached to the eye 302 (shown in the figure as a sphere representing the eye). The outer sealing member 303 is engaging the eye 302. The interface device has a distal section 304, which is closest to the eye 302 and a proximal section 305, which is closest to the laser.

A handle 306 is attached to the interface device 301 to assist in place the device on the eye 302. In this embodiment the distal section 304 is much smaller and a different shape than the proximal section 305. In this manner the distal section 304 can fit in most eye openings (between the eye lids), while the larger proximal section 305 has the size needed to provide features such as larger beam path, mounting of handle, attachment to engagement arm, and reservoir of fluids.

Figure 4A:
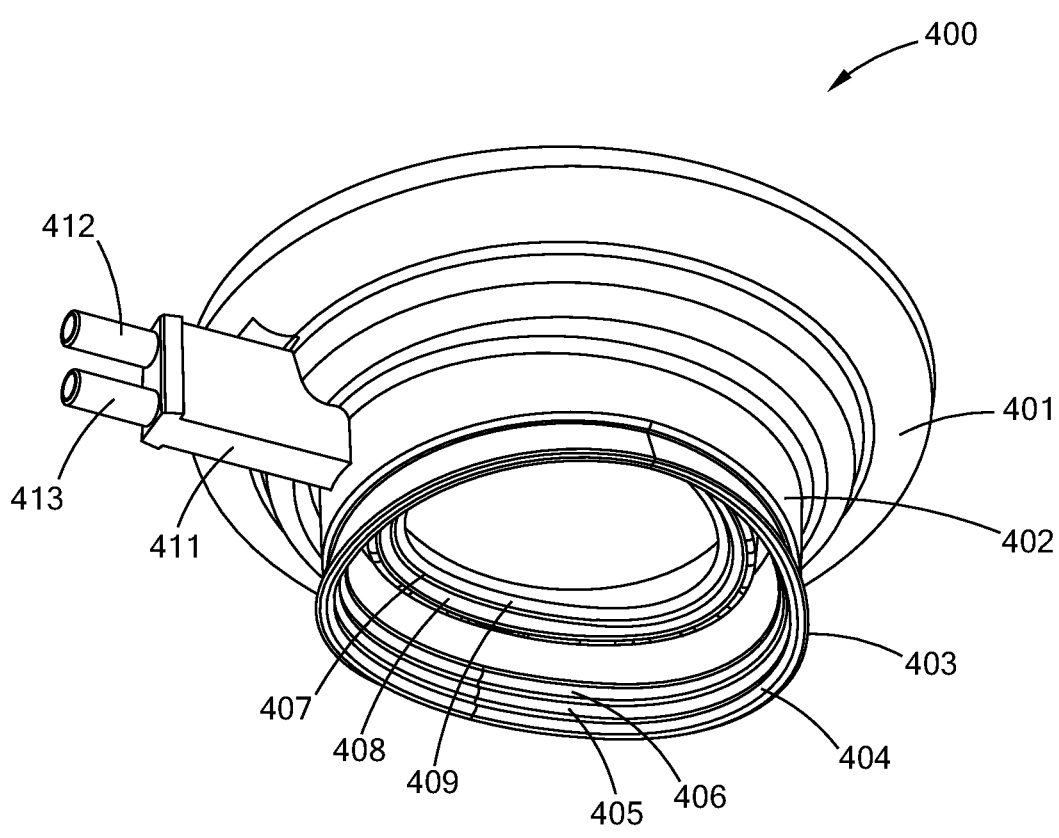
FIGS. 4A, 4B and 4C, there are provided a bottom perspective view, a top plan view, and top perspective view, respectively of an embodiment of an interface device in accordance with the present inventions.
Figure 4B:
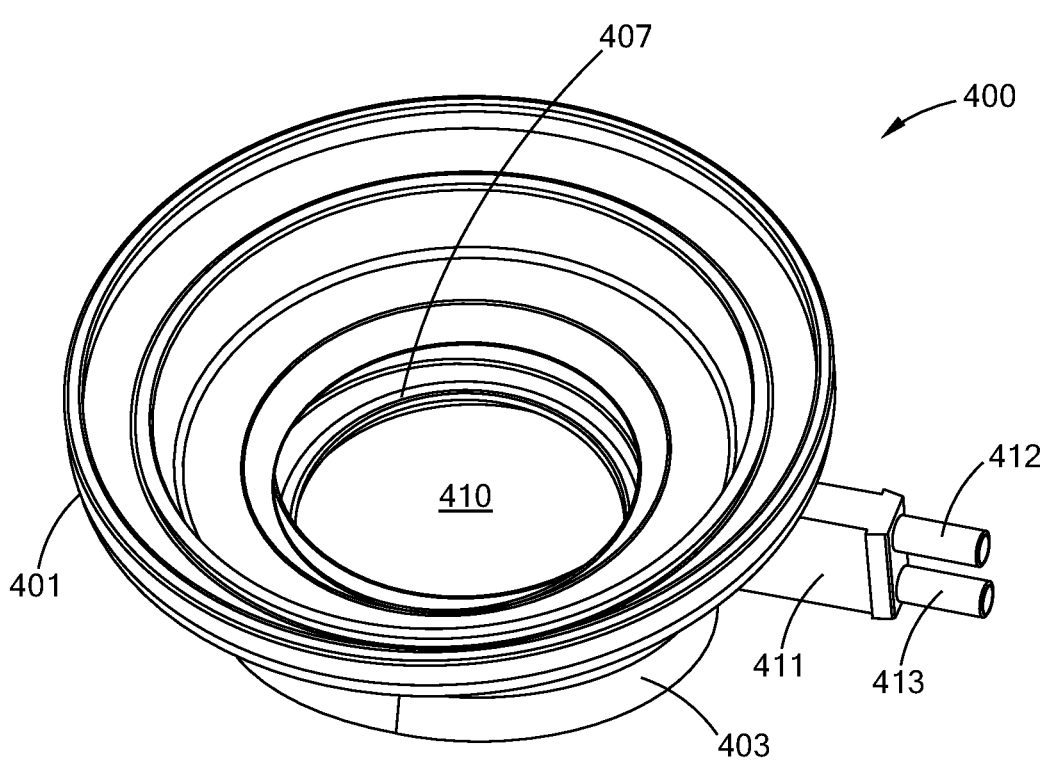
Figure 4C:
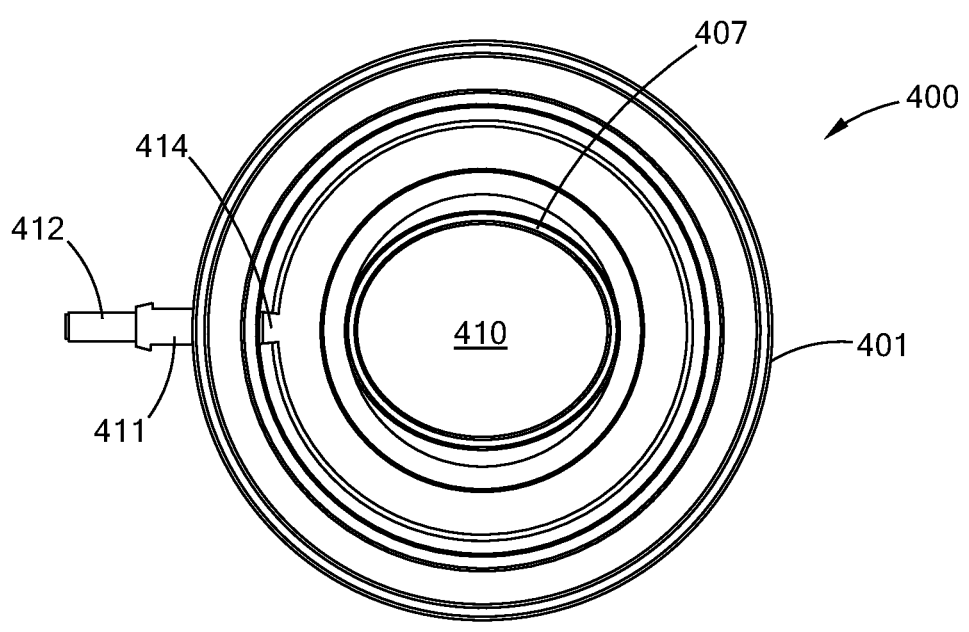

Turning to FIGS. 4A, 4B and 4C, there are provided a bottom perspective view, a top plan view, and top perspective view, of an embodiment of an interface device 400. The interface device 400 has a proximal section 401, which has a circular outer shape and inner opening; and a distal section 402, which has an oval outer shape and inner opening. It has an outer sealing member or lip 403 that has three sealing ridges 404, 405, 406. It has an inner sealing member or lip 407 that has two sealing ridges 408, 409. The inner opening 410 is oval like, and is in the distal section 402, which has an oval like outer shape. The device 400 has a port 411 having two line connectors 412, 413, and an opening 414

(shown in FIG. 4C). The embodiment of FIG. 4A, 4B, 4C does not have a window, lens or other covering over the opening 410.

It being under stood that, in this and other embodiments, more or less ridges can be used, that more or less ports and openings can be used.

In this embodiment opening 414 is connected with, e.g., in fluid communication with line 412, and is used to fill the opening with fluid (e.g., saline) after the device has been affixed to the eye. The lower line, 413 is used to remove air from the channel between the sealing members, creating a reduced pressure zone to hold the device on the eye.

Figure 5:
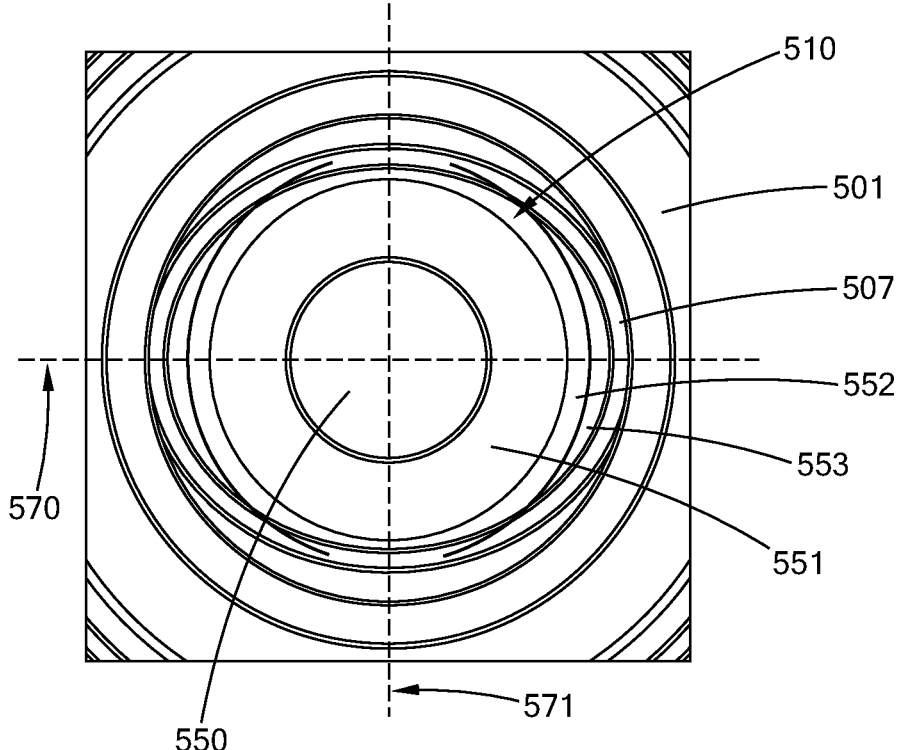
FIG. 5 is a top plan view of an embodiment of an interface device engaged on an eye in accordance with the present inventions.

Turning to FIG. 5 there is shown a top plan view of an interface device engaged on an eye. The interface device has a major axis 570, which corresponds to the nasal-temporal axis of the eye, and a minor axis 571, which corresponds to the vertical axis of the eye. Looking into the opening 501 of the device, the pupil 550, the iris 551, the limbus 552, and sclera 553 are revealed.

It should be noted that in this embodiment the outer edge of the limbus 552 and some of the sclera 553 are revealed in the opening 510 along the major axis 570, while the outer edge of the limbus 552 and the sclera 553 is not reviewed along the minor axis 571 of the opening 510.

Figure 6A:
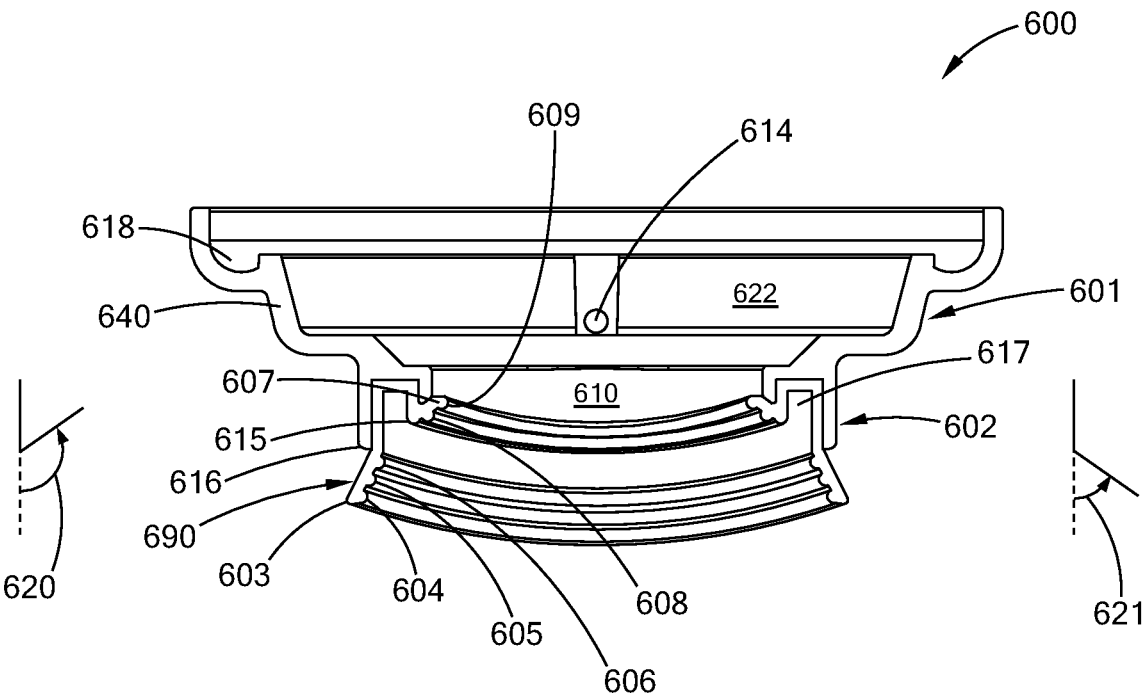
FIGS. 6A, 6B, and 6C there is shown respectively a cross section along the minor axis, a cross section along the major axis, and a perspective (engaged with the eye) cross section along the major axis of an embodiment of an interface device in accordance with the present inventions.
Figure 6B:
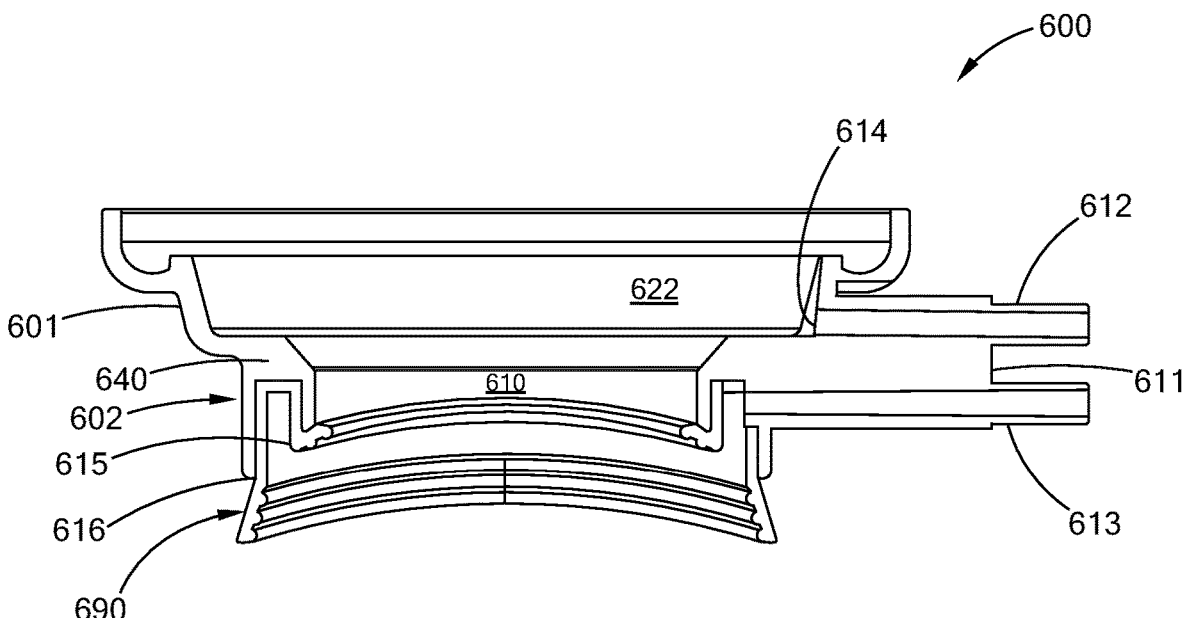
Figure 6C:
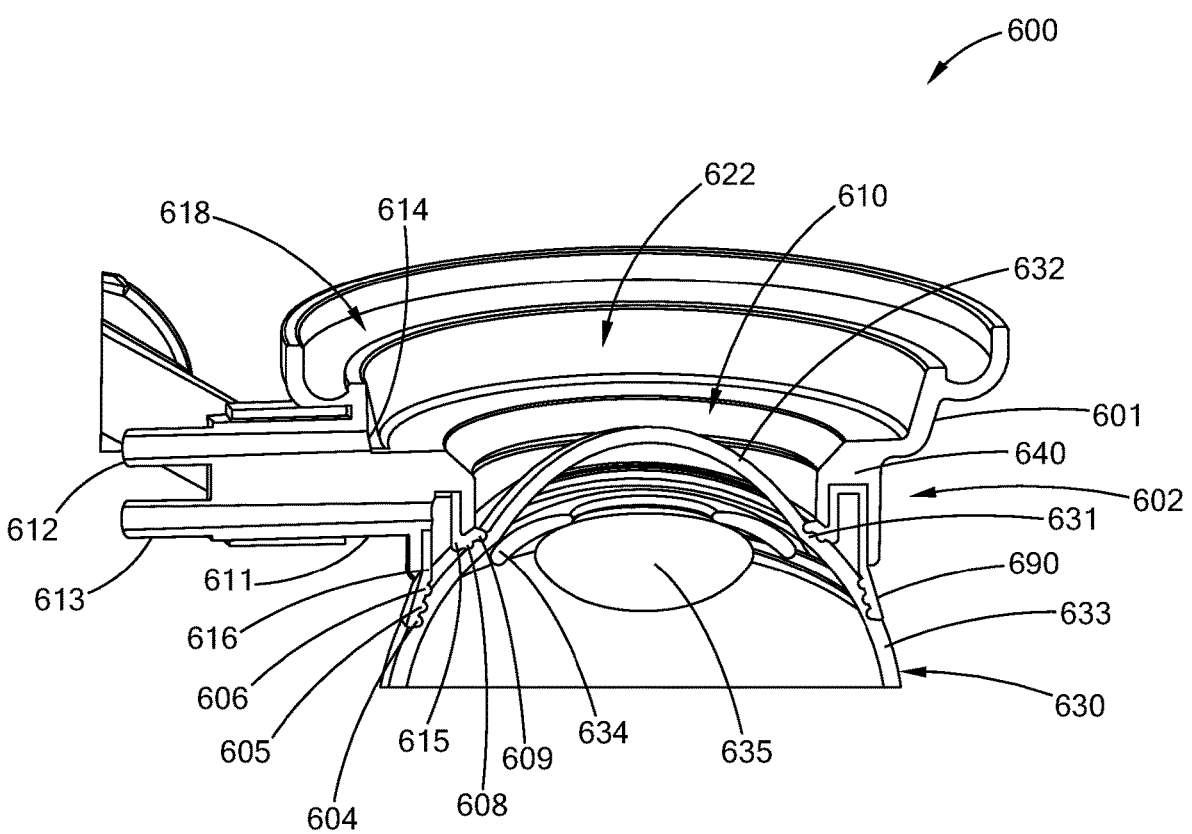

Turning to FIGS. 6A, 6B, and 6C there is shown respectively a cross section along the minor axis, a cross section along the major axis, and a perspective (engaged with the eye) cross section along the major axis of an embodiment of an interface device.

The interface device 600 has a proximal section 601 and a distal section 602. It has an outer sealing member or lip 603 that has three sealing ridges 604, 605, 606. It has an inner sealing member or lip 607 that has two sealing ridges 608, 609. The inner opening 610 is an oval, the ratio of major to minor axes for the open 610 is larger in the distal section 602 than in the proximal section 601. (In this manner the opening is rounder, e.g., more circular, in the proximal section 601 than in the distal section 602.) The device 600 has a port 611 having two line connectors 612, 613. Line 612 connects to opening 614 and is used to fill the fluid chamber 622 with a liquid, e.g., saline, the fluid chamber 622 has an overflow channel 618. In this embodiment the device does not have a window, lens or other covering over the opening 610. It being under stood that more or less ridges can be used, that more or less ports and openings can be used.

The device has a ridged structure or housing 640, that forms both the proximal section 601 and a portion of the distal section 602 of the device 600. The ridged housing 640 has a flexible insert 690. The flexible insert 690 is in direct contact with the ridged housing 640 and has the inner sealing member 607 and the outer sealing member 603 and forms the vacuum cavity 617. Line 613 is connected to and is in fluid communication with vacuum cavity 617. (It being understood that the term "vacuum cavity" in this context refers to a reduced pressure cavity that is used to affix or hold the device to the eye). Preferably, in this embodiment, the flexible insert 690 is the only part of the device 600 that directly contacts the surface of the eye 630.

As shown in FIG. 6A, the contact member angle for the inner member 607 is shown by arrow 620; and the contact member for the outer member 603 is shown by arrow 621. In this embodiment the contact member angel 620 is greater than 90°, and is about 125°. In this embodiment, the contact member angle 621 is less than 90°, and is about 50°. Thus, the end of the sealing member 607 is pointing, e.g., directed upward, proximally, and somewhat away from the eye. The flexible insert 690 has a first hinge section 615 for the inner sealing member 607, and a second hinge section 616 for the outer sealing member 603.

In embodiments of the general type shown in FIGS. 6A-C, and other embodiments, the contact member angel for the inner member is greater than 90°, and can be from about 95° to about 175°, can be from about 105° to about 155°, can be from about 115° to about 135°, can be from about 123° to about 137°, and can be from about 125° to about 135°, other angles are also contemplated, as well as, angles smaller than 90°. In embodiments of the general type shown in FIGS. 6 A-C, and other embodiments, the contact member angel for the outer member is member is less than 90°, and can be from about 5° about 85°, can be from about 20° about 70°, can be from about 5° about 85°, can be from about 40° about 60°, can be from about 30° about 40°, can be from about 34° about 46°, other angles are also contemplated, as well as, angles larger than 90°. In general, depending upon the stiffness of the material, the flexibility of any hinge, the angle of the sealing members, e.g., contacting members, should be such as to engage and form to the surface of the eye in a non-damaging, and preferably nonirritating manner, and then hold and maintain the reduced pressure to fix the device to the eye during the procedure.

Comparing FIGS. 6A and 6B (non-engaged) with FIG. 6C (engaged) the sealing members move, change shape, as the device contacts, engages and then is affixed to the eye. The inner member 607 (along the major axis) is not contacting the limbus 631, and is contacting and sealing against the sclera 633. The outer member 603, (along the major axis) is further away from the limbus 631, and is contacting and sealing against the sclera 631. The structures of the eye 630, the limbus 631, the cornea 632, the sclera 633, the iris 634 and the pupil 635 are shown with respect to the device 600. Along the major axis the opening 610 is larger than the outer diameter of the iris 634, and the inner 607 and outer 603 sealing members are positioned outside of the iris 634.

The average diameter of the limbus (i.e., the inner limbus-cornea boundary) is about 12 mm. Thus, in embodiments of the type show in FIGS. 6 A-C, as well as other types of embodiments, the inner opening, prior to engagement, along the major axis can be from abut 11.8 mm to about 15 mm, about 12.1 mm to about 14.5 mm, about 12.3 to about 13.8 mm, about 12.9 mm to about 13.9 mm, and about 12.2 mm to about 13.3 mm. The diameter of the inner opening formed by the inner member, when engaged against the eye, along the major axis can be from about 11.8 mm to about 15 mm, about 12.1 mm to about 13.9 mm, about 12.7 mm to about 13.8 mm, about 12.9 mm to about 13.8 mm, and about 12.2 mm to about 13 mm. Larger and smaller, and combinations and variations of these sizes, for both unengaged and engaged openings along the major are contemplated.

In embodiments of the type show in FIGS. 6 A-C, as well as other types of embodiments, the inner opening, prior to engagement, along the minor axis can be from abut 10.8. mm to about 12.2 mm, about 11 mm to about 12 mm, about 11.3 to about 11.8 mm, about 11.5 mm to about 12.1 mm, and about 11.3 mm to about 11.9 mm. The diameter of the inner opening formed by the inner member, when engaged against the eye, along the major axis can be from about 10.6 mm to about 12.2 mm, about 11.3 mm to about 11.8 mm, about 11.6 mm to about 12 mm and, about 11.4 mm to about 11.8 mm, and about 11.5 mm to about 11.8 mm. Larger and smaller, and combinations and variations of these sizes, for both unengaged and engaged openings along the major are contemplated.

The flexible insert, which includes the contact members, can be made from any flexible material that is safe for direct contact with the eye.

In this manner embodiments of the interface device engage several different structures of the eye, e.g., the limbus, the cornea and the sclera.

The shape, design and contact member angle(s) of the sealing members, as well as, the amount and sequence (e.g., high initial and then less upon sealing) of applying the vacuum (e.g., reduced pressure) can be predetermined for contact with one, two or all of these outer structures of the eye. Thus, in embodiments of the devices, the device can be in 100% engagement with the limbus, 100% engagement with the sclera, and in 100% engagement with the cornea, and combinations and variations of these along the major and minor axes.

In a preferred embodiment, the inner member, along the major axis, engages the sclera, and does not engage the limbus or the cornea; and the inner member along the minor axis engages the limbus and does not engage the sclera. The outer member engages the sclera along the entirety of its length.

In an embodiment, the ratio of the minor axis to the major axis for the opening formed by the inner member (engaged or unengaged) can be, for example, about 1:1.1, about 1:1.13, about 1:1.15, about 1:1.17, about 1:1.18, from about 1:1.1 to about 1:1.3, from about 1:1.13 to about 1:1.25, and from about 1:1.15 to about 1:1.2, larger and smaller ratios may also be used.

In an embodiment the major and minor axis can be the same, i.e., the ratio is 1:1, e.g., a circle.

In general vacuum pressures can be from about 150 mmHg to about 250 mmHg, and for example the vacuum can be about 190 mmHg and less, can be about 180 mmHg and less, can be about 220 mmHg and less, and can be about 210 mmHg and less. (In this context "less" vacuum, or "reducing the vacuum" means more pressure or higher pressure is present.)

In embodiments of the device, the initial pressures, for initial sealing can be about 180 mmHg, about 190 mmHg, about 220 mmHg, from about 150 mmHg to about 220 mmHg, from about 185 mmHg to about 250 mmHg, and from about 185 mmHg to about 230 mmHg, and other pressures. In embodiments of the device these initial reduced pressures can be reduced (i.e., the amount of suction is reduced, and the pressure is increased), to the pressures used during the procedure, e.g., a holding pressure, which can be about 185 mmHg, about 190 mmHg, about 205 mmHg, from about 175 mmHg to about 245 mmHg, from about 185 mmHg to about 220 mmHg and from about 205 mmHg to about 250 mmHg, and other pressures.

The shape and size of the eye piece and the engagement members permit a lower pressure to be used during initial sealing and then be maintained at this lower pressure during the proceeding. This pressure can be about 180 mmHg, about 200 mmHg, from about 180 mmHg to about 225 mmHg, and from about 205 mmHg to about 250 mmHg.

The reduced pressure zone in the embodiment of FIG. 6, as well as other embodiments, is in the these shape, i.e., the area on the eye of the reduced pressure zone has a shape, of a non-planar ellipse.

Figure 7:
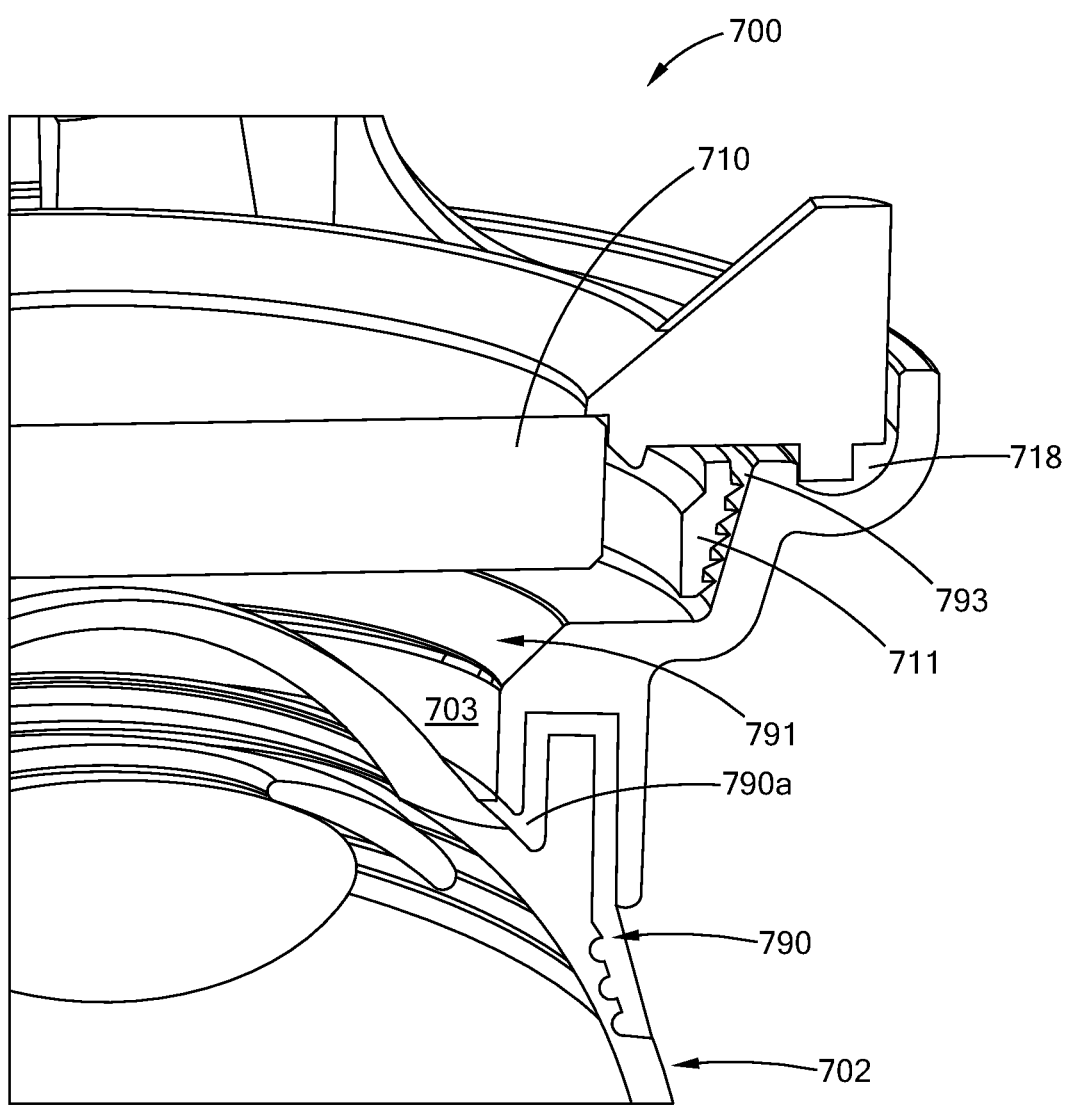
FIG. 7 there is provided a cross sectional view of a portion of an embodiment of an interface device in accordance with the present inventions.

Turning to FIG. 7 there is provided a cross sectional view of a portion of an elliptical shaped embodiment of an interface device 700 engaged on the surface of an eye 702. The interface device 700 has a fluid chamber 791 that has a baffle ring 711, and an overflow channel 718. The fluid chamber 791 is not completely sealed. It has a window 710 covering the top of the chamber 791 (e.g., generally over the eye and extending outwardly beyond the opening 703. The bottom of the fluid cavity 791 is sealed against the surface of the eye by the inner flexible sealing member 790a and an outer flexible sealing member 790. The fluid cavity 791 is in fluid communication with and has a fluid channel 793 that extends from the fluid chamber 791, past the baffle ring 711, and to overflow channel 718, which overflow channel 718 is preferably not covered or sealed. In this manner if the opening 703 (and the fluid chamber 791) is filled with too much fluid, it will not increase pressure on the eye. Instead, any excess will over flow out of overflow channel 718 and drain down the outside of the device 700.

Figure 8:
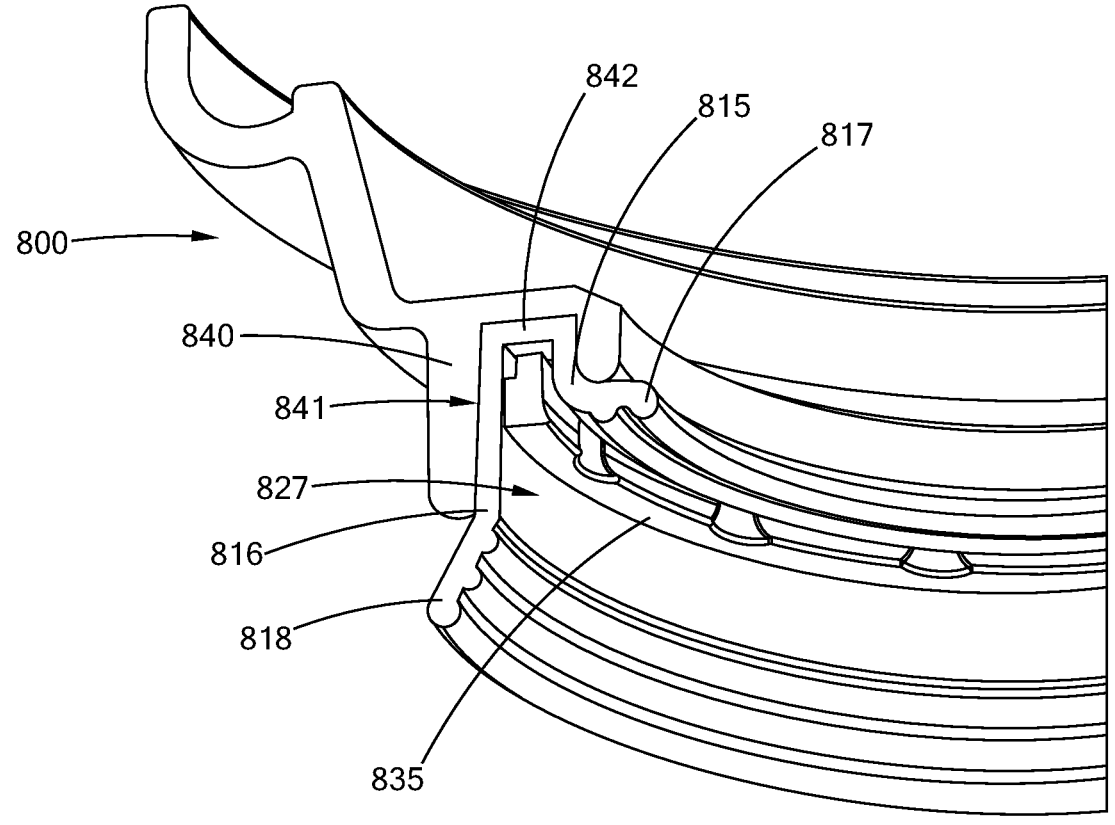
FIG. 8 there is provided a cross sectional view of a portion of an embodiment of an interface device in accordance with the present inventions.

Turing to FIG. 8 there is a cross sectional view of a portion of an elliptical shaped embodiment of an engagement device 800. The engagement device 800 has a rigid structure 840 forming and engagement channel 841 for receiving and holding the flexible member 842. Flexible member 842 is seated in, and preferably held in channel 841. The flexible member can be held by way of for example a friction fit, detent, glue, and other appropriate means, and combinations and variations of these and other manners of attachment. The flexible member 842 has hinge section 816 and hinge section 815, which connect to flexible sealing members (e.g., contacting members, engagement members) 818, 817. In this embodiment the hinge members are located adjacent to the lower portions (e.g., the ends) of the channel 841. In FIG. 8 the flexible members 818, 817 are shown in the unengaged position. The flexible member 842 forms a vacuum channel 827 (e.g., a channel that will have a vacuum of predetermined amount applied to it, to provided an area, e.g., ring, of reduced pressure adjacent to the surface of the eye). There is also present in the vacuum channel 827 a baffle ring 835. The ring 835 is a vacuum distribution enhancement ring. This ring reduces the stress that is placed on the conjunctiva membrane and has the ability to reduce, make less severe, and preferably prevent subconjunctival hemorrhage.

Generally, in embodiments where a ridged channel is formed to hold a flexible inner member, the sealing flexible member or members, can rotate in a semi-arcuate fashion around a point, or area, adjacent to the end of the ridged channel. In some embodiments this point or area of rotation can be viewed as a hinge or hinge area.

In embodiments the ridged channel need not be as ridged as the rest of the engagement device, or it may be more ridged than those other components. Generally, in embodiments where flexible members are used, and in particular where the flexible members are not an integral part of the interface device as a whole, the ridged channel should be of a material that has sufficient properties to enable docking and maintaining the device at a fixed location with respect to the laser, as well as, having the necessary physical properties and shape (e.g., rigidity, hardness, and in some cases radius of curvatures near the hinge areas) to permit the flexible members to deflect or otherwise move as they engage the surface of the eye. In other embodiments where the flexible members are not required to move, and in particular not required to move in a semi-arcuate path around a hinge member, these consideration are of less importance, and these features need not be employed.

The device may be applied with a sufficient pressure that does not damage the eye. Once the device has been attached, and especially for longer procedures, the attachment pressure can be increased (i.e., less suction) to reduce stress on the eye, while still keeping the device on the eye and keeping the seal against the eye to keep the fluid chamber from leaking. The vacuum amount profile over time can also be varied depending upon the section of the eye, and the relative areas of those sections that the vacuum area is affixed to.

Figure 9:
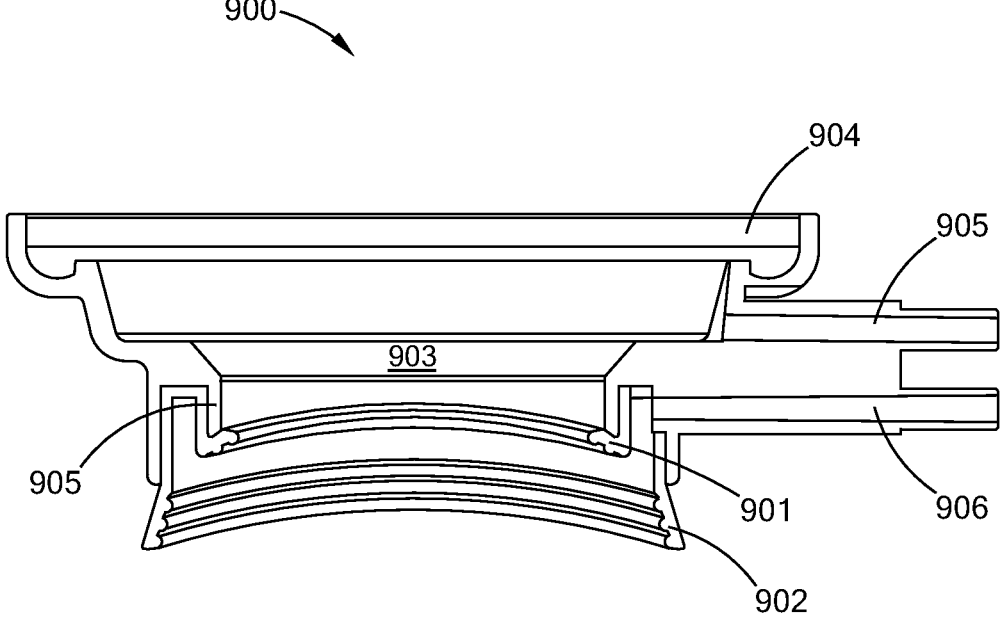
FIG. 9 there is shown a cross sectional view along the major axis of an embodiment of an interface device in accordance with the present inventions.

Turning to FIG. 9 there is shown a cross sectional view of an embodiment of an interface device 900 along the major axis. The device 900 has an overflow channel 904, an opening 903, a ridged member 905, an inner sealing member 901 (which has a contact member angle of greater than 90°), and an outer sealing member 902, which has a contact member angle of less than 90°. There is also provided a fluid inlet line 905 and a vacuum line 906. In this embodiment the opening to the eye is not covered, there is no window, contact lens, applanater, or other covering over the opening.

Figure 10:
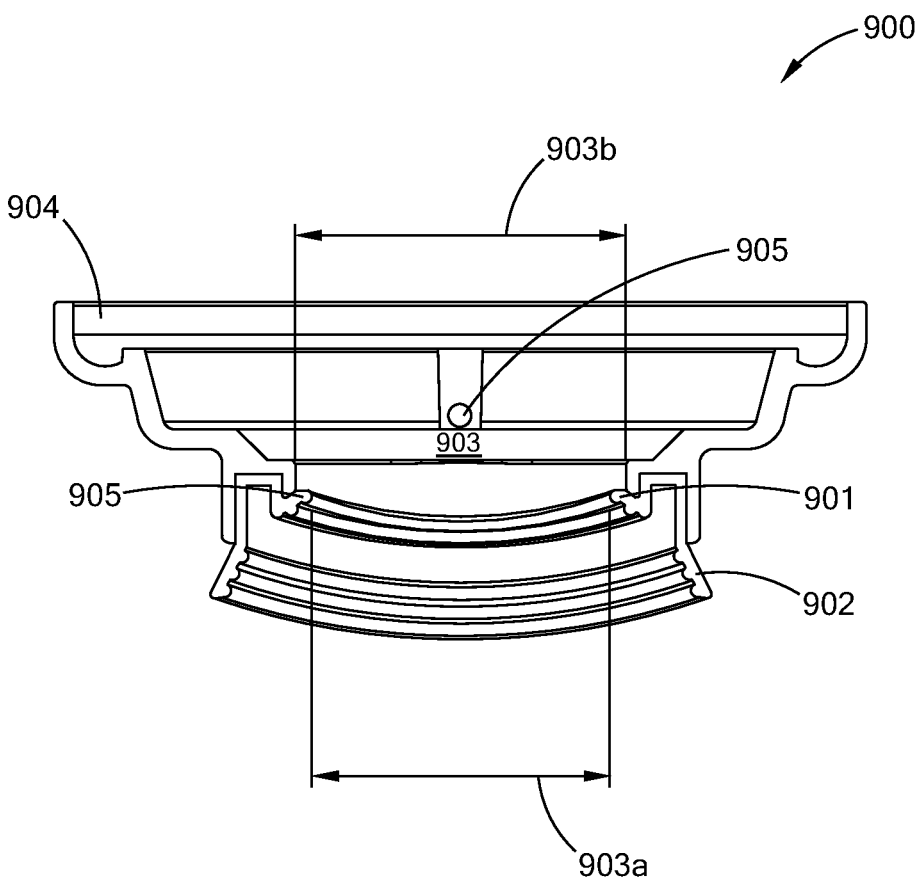
FIG. 10 there is shown a cross sectional view along the minor axis of the device of FIG. 9.
Figure 11A:
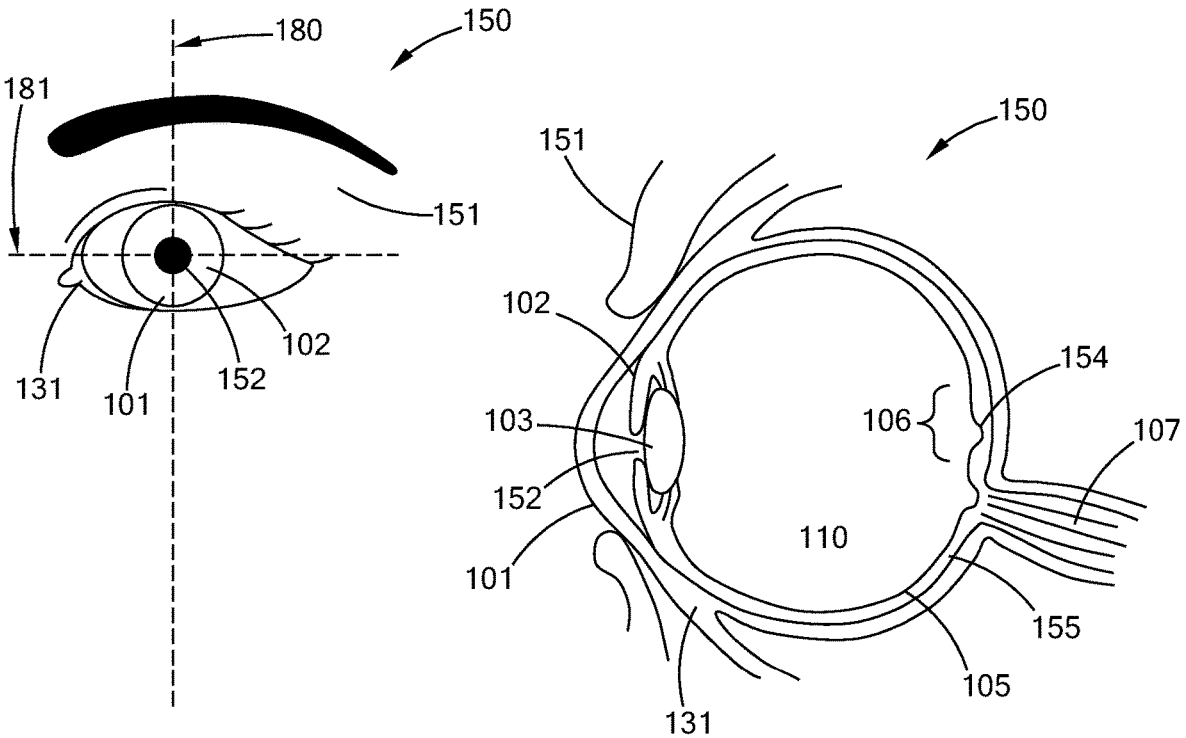
FIGS. 11A, 11B and 11C are cross sectional view of structures of the eye.
Figure 11B:
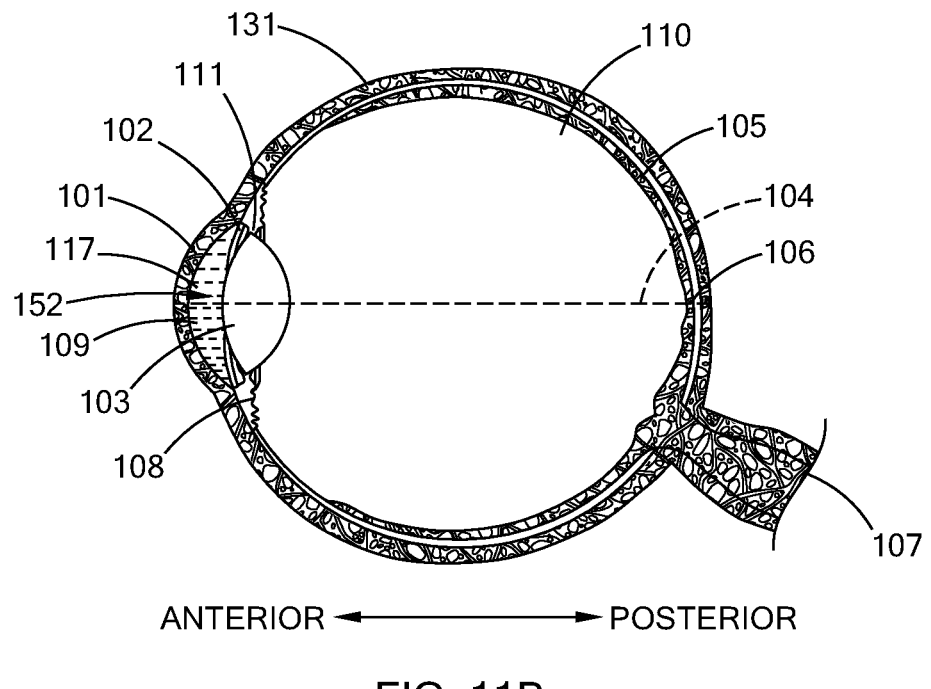
Figure 11C:
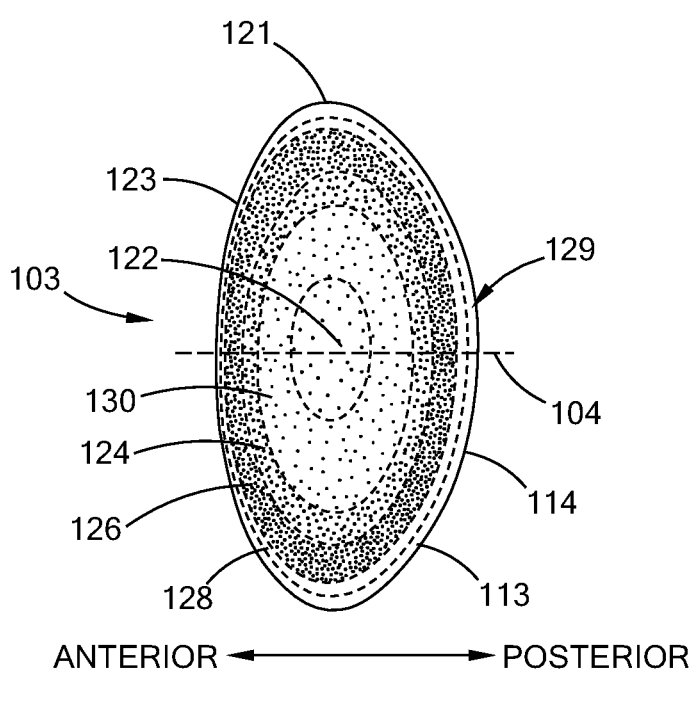

FIG. 10 is a cross sectional view of the device 900 of FIG. 9 taken along the minor axis (like numbers indicate like structures). In this figure the size of the opening 903, as formed by the ridge member 905 is shown by arrow 903b; and the size of the open 903 as formed by the inner flexible member 901 is shown by arrow 903a. Thus, it can be seen that the diameter of the opening formed by the inner contact member of the flexible member is smaller than the diameter of the opening formed by the rigid member. This, difference in open diameter is also present along the major axis, and can be seen in the FIG. 9.

The fluids that can be used include saline, as well as, index matching fluids, such as those provided by U.S. patent application Ser. No. 12/840,818. These fluids may also contain medicaments or therapeutic agents such as analgesics, local anesthetics, or mydriatics.

Figure 12:
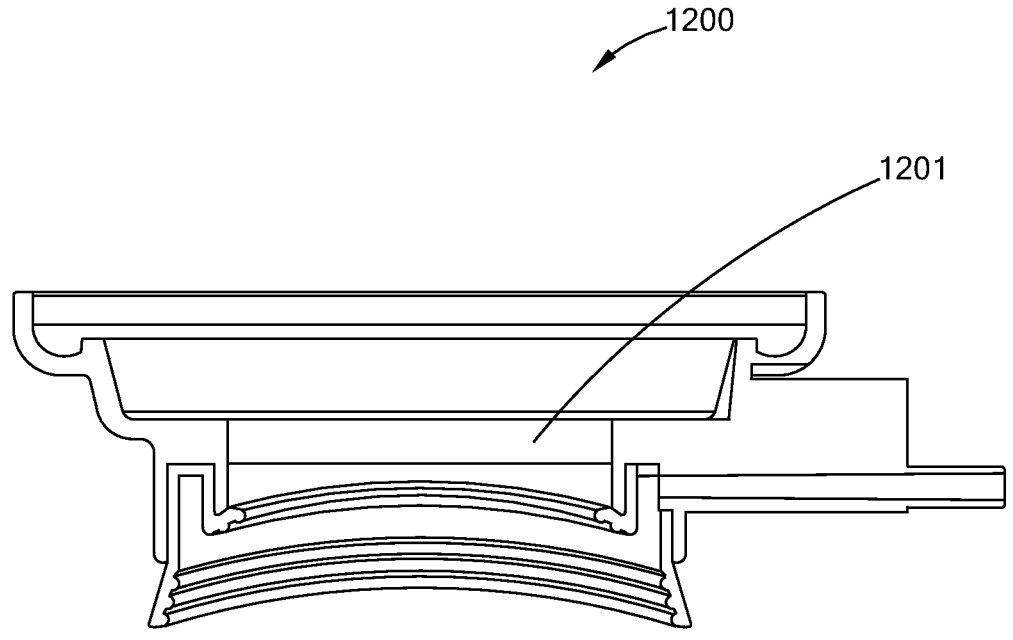
FIG. 12 is a cross sectional view on an embodiment of an interface device in accordance with the present inventions.

FIG. 12 is a cross sectional view of an interface device 1200 having a flat application window 1201. This device is intended to applinate the cornea upon engagement to provide a flat (e.g., essentially planar, and preferable planar) corneal surface, as the cornea is engaged against and flattened by the window 1201. (The other structures of the device 1200 are similar to the other embodiments of the device taught in this specification).

Figure 13:
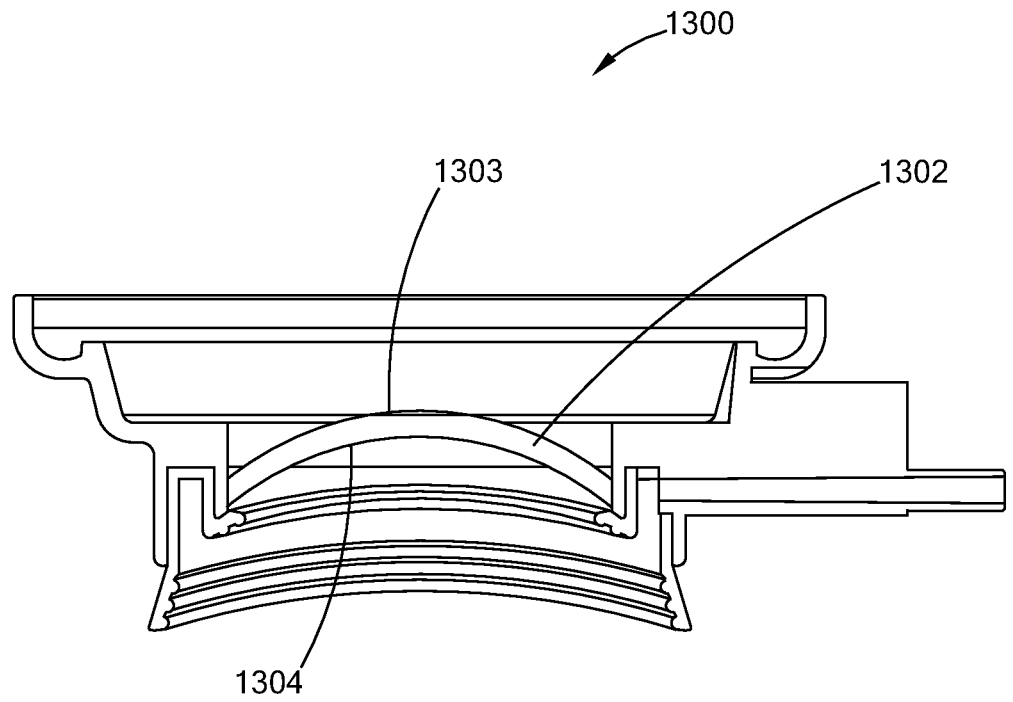
FIG. 13 is a cross sectional view on an embodiment of an interface device in accordance with the present inventions.

FIG. 13 is a cross sectional view of an interface device 1300 having a curved application window 1302. The application window 1302 has an upper surface 1303 and a lower surface 1304. Preferably, the thickness of the window is uniform (i.e., the arcs formed by the upper and lower surfaces have the same center point). In this manner the curved application window provides a predetermined optical property, e.g., power, to the laser beam and optical paths through the opening of the device. Upon engagement, the surface of the cornea engages against surface 1304 and is forced to conform to the radius of curvature of that surface. The arcs of the upper and lower surfaces may be different, the center points may be different and these other combinations to provide a curved application window with a predetermined optical property. This device is intended to applinate the cornea upon engagement to provide a known and predetermined curvature to the cornea as the cornea is engaged against and shaped by the window 1302. (The other structures of the device 1300 are similar to the other embodiments of the device taught in this specification).

Figure 14:
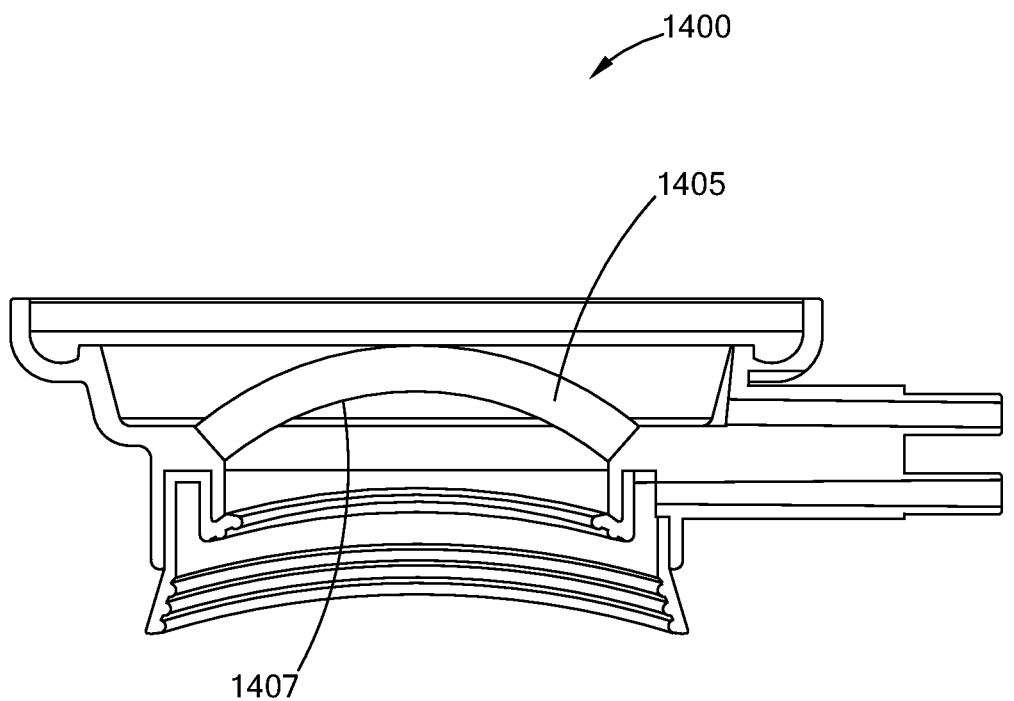
FIG. 14 is a cross sectional view on an embodiment of an interface device in accordance with the present inventions.

FIG. 14 is a cross sectional view of an interface device 1400 having a non-applinating curved window 1405. In this embodiment upon engagement the window lower surface 1407 does not engage the cornea.

Thus, the window 1405 does not change or alter the shape of the cornea when the device is engage against eye. The arc and shape of the window may also be such that it essentially follows the shape of the cornea, for example like a properly fitted contact lens, and thus, although it is in contact with the surface of the cornea, does not significantly change the shape of the cornea (e.g., along the lines of the minor changes that may occur from wearing a properly fitted contact lens), and preferable does not change the shape of the cornea. (The other structures of the device 1400 are similar to the other embodiments of the device taught in this specification).

Figure 17:
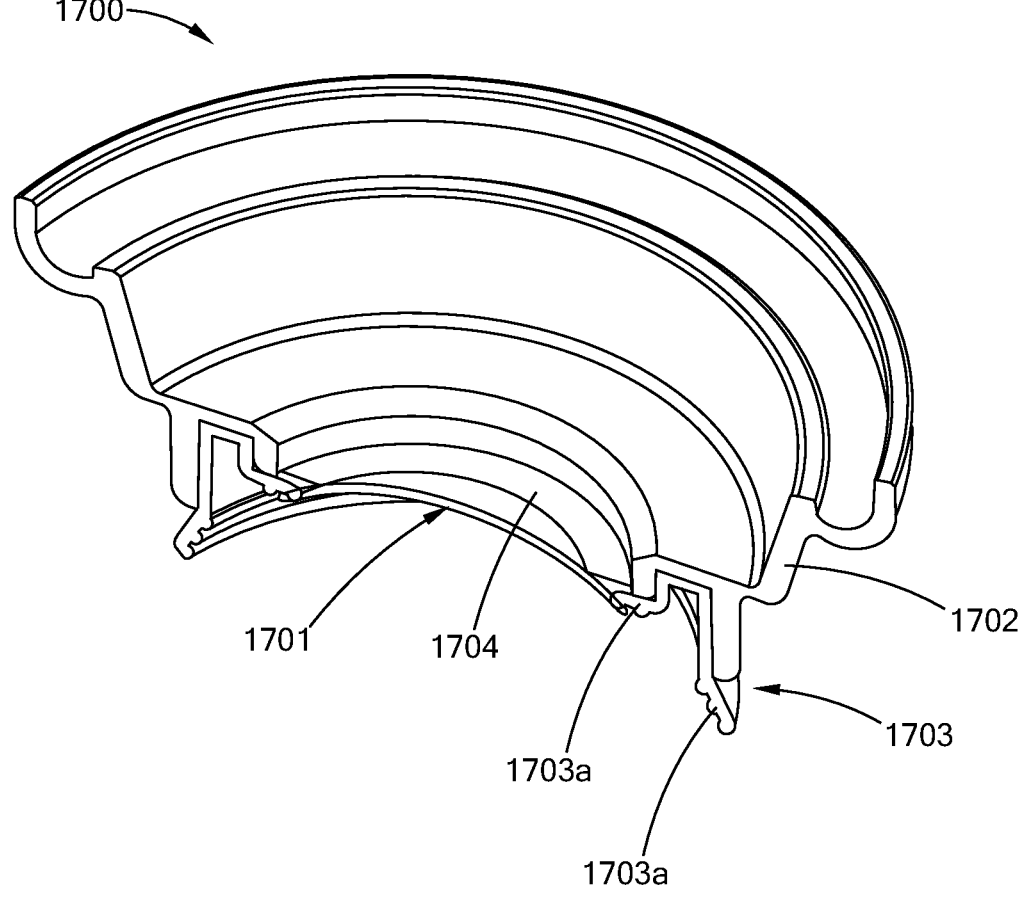
FIG. 17 is a cross section perspective view of an embodiment of an interface device in accordance with the present inventions.

Turing to FIG. 17 there is shown a cross section perspective view on an embodiment of an interface device 1700. The interface device 1700 is an elliptical configuration, having a ridged channel 1702 for holding a flexible engagement member 1703, having an inner engagement member 1703a and an outer engagement member 1703b. A curved window 1701, e.g., a contact lens, is attached to the interface device 1700 by a flexible rind 1704. The flexible ring 1704 is attached to the ridged channel 1702 and the curved window 1701. In this embodiment the inner engagement member 1703a is adjacent to the flexible ring 1704. The window 1701 is attached to the flexible ring 1704. The flexible ring 1701 can be attached to the ridged channel 1702 and the contact lens by glue, or other suitable attachment techniques.

In embodiments the flexible ring can be attached to the inner engagement member, to the inner surface of the opening, or to one or more other structures or attachment points, e.g., ledge, slot, surface, etc., on the interface device, and combinations and variations of these. The embodiment of FIG. 17 is shown using a curved window, it should be understood that the flexible ring attachment configuration can be used with planar windows, curved application windows, curved non-application windows, and other types of windows.

An example of an embodiment of the device when used in a PID for an ophthalmic laser system can have the following features: distal end inner and outer members form a non-planar elliptical opening. The opening has an ID 11:7 mm×13.76 mm, and the distal end has an OD of 18.69 mm×20.82 mm. The non-planar ellipse forms a reduced pressure zone on the surface of the eye, having an area (surface area on the eye) of 258.1 mm$^2$.

The surface areas of the non-planar reduce pressure zones formed on the surface of the eye between the inner and outer engagement members, when engaged with the eye, can be, for example from 220 mm$^2$ to about 270 mm$^2$, and from about 235 mm$^2$ to about 265 mm$^2$.

As noted above embodiments of the present inventions can be sued with most laser eye surgery, or ophthalmic systems. Thus, for example, embodiments of the present inventions can be used in methods and and with systems for determining the shape and position of the natural human crystalline lens and cornea relative to a laser device so as to provide an enhanced method and system for applying a laser to the lens and cornea. For example, they can be used in methods and with systems that provide predetermined, precise and reproducible laser shot patterns that are reproducible from patient to patient and surgeon to surgeon. Embodiments of the present invention can additionally be used in methods and systems that determine, e.g., grade the degree of a cataract, determine the relative location within the lens of different levels of opacifications, determine the relative location within the lens of different levels of increased density, e.g., different levels of hardness, compaction, toughness of the natural lens, increased density, and compaction, and provide a laser beam of varying power, with the power being predetermined to correspond to the degree of increased density, e.g., a predetermined shot pattern having specific, and varied in a predetermined manner, laser powers that correspond to the determined density, grade or other material properties of the lens.

Figure 15:
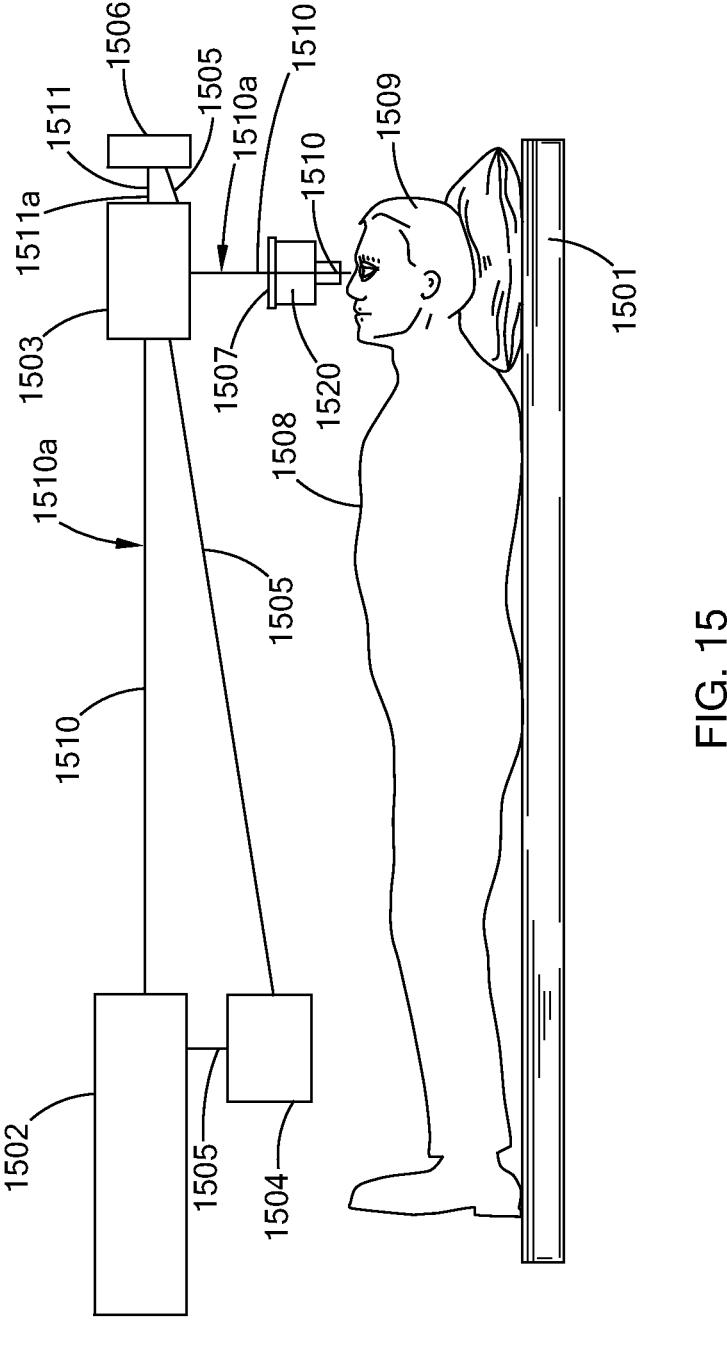
FIG. 15 is a schematic of an embodiment of a laser system with an embodiment of an interface device in accordance with the present inventions.

Thus, for example, embodiments of the present interface device can be used with a of a laser systems, an example of a general embodiment of which is illustrated in the schematic of FIG. 15. As generally shown in the embodiment of FIG. 15 there is provided a system for delivering a laser beam shot pattern to the lens of an eye comprising: a patient support 1501; a laser 1502; optics 1503 for delivering the laser beam 1510 along laser beam path 1510a; a control system for delivering the laser beam to the lens in a particular pattern 1504, which control system 1504 is associated with and/or interfaces with the other components of the system as represented by lines 1505; a means for determining the position of lens with respect to the laser 1506, which means 1506 receives an image 1511, along an image path, of a structure(s) of the eye; and a laser patient interface 1507, which includes an embodiment of the present interface devices. (It is noted that, solely for illustrative purposes, the block diagram of FIG. 15 does not show the interface engaged with the laser system, and does not show the interface engaged with the eye.)

The patient support 1501 positions the patient's body 1508 and head 1509 to interface, through interface device 1520 with the optics 1503 for delivering the laser beam 1510.

In general, the laser 1502 should provide a beam 1510 that is of a wavelength that is capable of being transmitted through one or more of the cornea, aqueous and lens, depending upon among other things the fluence of the beam a at a particular location or structure. The beam should be of a short pulse width, together with the energy and beam size, to produce photodisruption, including Laser Induced Optical Breakdown (LIOB). Thus, as used herein, the term laser shot or shot refers to a laser beam pulse delivered to a location that results in photodisruption. As used herein, the term photodisruption essentially refers to the removal or softening or changing of material through its interaction with light, e.g., a laser beam, and its resulting conversion to a different state, and should be given its broadest possible meaning herein, unless expressly stated otherwise. For example, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz.

Generally, lower pulse rates correspond to higher pulse energy in commercial laser devices. A wide variety of laser types can be used to cause photodisruption of ocular tissues, dependent upon pulse width and energy density. Thus, examples of such lasers would include: the Delmar Photonics Inc, Trestles-20, which is a Titanium Sapphire (Ti: Sapphire) oscillator having a wavelength range of 780 to 840 nm, less than a 20 femtosecond pulse width, about 100 MHz PRF, with 2.5 nanojoules; the Clark CPA-2161, which is an amplified Ti:Sapphire having a wavelength of 775 nm, less than a 150 femtosecond pulse width, about 3 KHz PRF, with 850 microjoules; the IMRA FCPA (fiber chirped pulse amplification) μjewel D series D-400-HR, which is a Yb:fiber oscillator/amplifier having a wavelength of 1045 nm, less than a 1 picosecond pulse width, about 5 MHz PRF, with 100 nanojoules; the Lumera Staccato, which is a Nd:YVO4 having a wavelength of 1064 nm, about 10 picosecond pulse width, about 100 KHz PRF, with 100 microjoules; and, the Lumera Rapid, which is a ND:YVO4 having a wavelength of 1064 nm, about 10 picosecond pulse width, and can include one or more amplifiers to achieve approximately 2.5 to 10 watts average power at a PRF of between 25 kHz to 650 kHz and also includes a multi-pulsing capability that can gate two separate 50 MHz pulse trains. and, the IMRA FCPA (fiber chirped pulse amplification) pJewel D series D-400-NC, which is a Yb:fiber oscillator/amplifier having a wavelength of 1045 nm, less than a 100 picosecond pulse width, about 200 KHz PRF, with 4 microjoules. Thus, these and other similar lasers can be used a therapeutic lasers.

In general, the optics 1503 for delivering the laser beam 1510 to the natural lens of the eye can be capable of providing a series of shots to the natural lens in a precise and predetermined pattern in the x, y and z dimension. The optics can also provide a predetermined beam spot size to cause photodisruption with the laser energy reaching the natural lens. Thus, the optics can include, for example: an x y scanner; a z focusing device; and, focusing optics. The focusing optics can be conventional focusing optics, and/or flat field optics and/or telecentric optics, each having corresponding computer controlled focusing, such that calibration in x, y, z dimensions is achieved. For example, an x y scanner can be a pair of closed loop galvanometers with position detector feedback. Examples of such x y scanners would be the Cambridge Technology Inc. Model 6450, the SCANLAB hurrySCAN and the ACRES Rhino Scanner. Examples of such z focusing devices would be the Phsyik International Peizo focus unit Model ESee Z focus control and the SCANLAB varrioSCAN.

In general, the control system for delivering the laser beam 1504 can be any computer, controller, and/or software hardware combination that is capable of selecting and controlling x y z scanning parameters and laser firing. These components can typically be associated at least in part with circuit boards that interface to the x y scanner, the z focusing device and/or the laser. The control system can also, but does not necessarily, have the further capabilities of controlling the other components of the system as well as maintaining data, obtaining data and performing calculations. Thus, the control system can contain the programs that direct the laser through one or more laser shot patterns.

In general, the means for determining the position of the lens with respect to the laser 1506 can be capable of determining the relative distance with respect to the laser and portions of the lens, which distance is maintained constant by the patient interface 1507. Thus, this component will provide the ability to determine the position of the lens with respect to the scanning coordinates in all three dimensions. This can be accomplished by several methods and apparatus. For example, x y centration of the lens can be accomplished by observing the lens through a co-boresighed camera system and display or by using direct view optics and then manually positioning the patients' eye to a known center. The z position can then be determined by a range measurement device utilizing optical triangulation or laser and CCD system, such as the Micro-Epsilon opto NCDT 1401 laser sensor and/or the Aculux Laser Ranger LR2-22. The use of a 3-dimensional viewing and measurement apparatus can also be used to determine the x, y and z positions of the lens. For example, the Hawk 3 axis non-contact measurement system from Vision Engineering could be used to make these determinations. Yet a further example of an apparatus that can be used to determine the position of the lens is a 3-dimension measurement apparatus. This apparatus would comprise a camera, which can view a reference and the natural lens, and would also include a light source to illuminate the natural lens. Such light source could be a structured light source, such as for example a slit illumination designed to generate 3-dimensional information based upon geometry. Further one, two, three, four or more, light sources can be positioned around the eye and the electronically activated to provide multiple views, plainer images, of the eye, and in particular the cornea and the lens, at multiple planar slices that can them be integrated to provide data for position and location information relative to the laser system about those structures.

In general, the laser 1502 provides (e.g., generates, propagates) a laser beam 1510, along laser beam path 1510a. The laser beam 1510 traveling along laser beam path 1510a travels through the optics 1503 and the interface device 1507, and through the opening 1520 in the interface device 1507 and enters the eye. There is also provided an image optical path, and an image optical signal 1511 (which may be coherent or non-coherent light) The image optical path and image optical signal 1511 travels along beam path 1510a, (thus at this point it is both an image optical path and a therapeutic laser beam path) until it reaches the optics 1503, where the image signal 1511 is directed along a different path 1511a to device 1506. Thus, the optical image beam path would include the beam path 1510a from the eye to the optics 1503 and then the path 1511a.

The various embodiments of devices, systems, configurations, components, activities, and operations set forth in this specification may be used with, in or by, various measuring, diagnostic, surgical and therapeutic laser systems, in addition to those embodiments of the Figures and disclosed in this specification. The various embodiments of devices, systems, configurations, components, activities, and operations set forth in this specification may be used with: other measuring, diagnostic, surgical and therapeutic systems that may be developed in the future: with existing measuring, diagnostic, surgical and therapeutic laser systems, which may be modified, in-part, based on the teachings of this specification; and with other types of measuring, diagnostic, surgical and therapeutic systems. Further, the various embodiments of devices, systems, laser shot patterns, activities, and operations set forth in this specification may be used with each other in different and various combinations. Thus, for example, the configurations and components provided in the various embodiments of this specification may be used with each other; and the scope of protection afforded the present inventions should not be limited to a particular embodiment, configuration or arrangement that is set forth in a particular embodiment, example, or in an embodiment in a particular Figure.

The inventions may be embodied in other forms than those specifically disclosed herein without departing from their spirit or essential characteristics. The described embodiments are to be considered in all respects only as illustrative and not restrictive.

What is claimed:

1. An interface device for fixing on a human eye and operably connecting to an ophthalmic therapeutic, monitoring, diagnostic, or evaluative device, the interface device comprising:

a. a body having an upper and a lower section, wherein the lower section defines a distal end of the interface device for contacting a surface of the eye and the upper section defines a proximal end of the interface device; whereby the proximal and distal ends define a device height along a vertical axis of the device;

b. the lower section of the body defining an outer shape;

c. the upper and lower sections of the body defining an opening through the device;

d. the device having a major and a minor axis, wherein when in use the major axis corresponds to a nasal temporal axis;

e. the lower section having an inner contact member surrounded by an outer contact member; the contact members each having a distal end; wherein the distal ends of the contact members form the distal end of the device; wherein the inner contact member defines an elliptical opening having a major and a minor axis; whereby the elliptical opening is an ellipse;

f. the inner contact member having a height, and the outer contact member having a height; and, g. wherein the height of the inner contact member varies between a point intersecting the major axis and a point intersecting the minor axis.

2. The device of claim 1, wherein the major axis of the opening at the distal end of the device is from about 1.01 to about 1.2 times larger than the minor axis.

3. The device of claim 1, wherein the major axis of the opening at the distal end of the device is from about 1.08 to about 1.21 times larger than the minor axis.

4. The device of claim 1, wherein the major axis of the opening at the distal end of the device is from about 1.15 to about 1.19 times larger than the minor axis.

5. The devices of claim 1, 2, 3, or 4, wherein the distal end of the inner contact member is shorter at the minor axis and taller at the major axis.

6. The devices of claim 1, 2, 3, or 4, wherein the distal end of the outer contact member is shorter at the minor axis and taller at the major axis.

7. The devices of claim 1, 2, 3, or 4, wherein the distal end of the inner contact member defines a shape of a non-planar ellipse.

8. The devices of claim 1, 2, 3, or 4, wherein the distal end of the outer contact member defines a shape of a non-planar ellipse.

9. The devices of claim 1, 2, 3, or 4, wherein the distal end of the inner contact member and the distal end of the outer contact member define a shape of a non-planar ellipse.

10. The devices of claim 1, 2, 3, or 4, wherein the inner contact member defines a contact member angle of greater than 90°.

11. The devices of claim 1, 2, 3, or 4, wherein the outer contact member defines a contact member angle of less than 90°.

12. The device of claim 1, comprising a window over the opening.

13. The device of claim 12, wherein the window is a curved window.

14. The device of claim 13, wherein the window is a contact lens.

15. The device of claim 13, wherein the curved window is configured so that when in use the curved window contacts the surface of the eye and changes the shape of the eye.

16. The device of claim 1, comprising a planar applanation window.

17. The device of claim 1, wherein the inner contact member is configured so that when in use the inner contact member contacts a sclera of the eye, and does not contact a limbus of the eye along the major axis.

18. The device of claim 1, wherein the inner contact member is configured so that when in use the inner member contacts the limbus at the minor axis.

19. The device of claim 1, wherein the opening is larger than a typical human iris, and thereby the device does not obstruct the iris.

20. An interface device for fixing on a human eye and operably connecting to an ophthalmic therapeutic, monitoring, diagnostic, or evaluative device, the interface device comprising:

a. a body having an upper and a lower section, wherein the lower section defines a distal end of the interface device for contacting a surface of the eye and the upper section defines a proximal end of the interface device; whereby the proximal and distal ends define a device height along a vertical axis of the device;

b. the lower section of the body comprising a ridged annular channel;

c. the ridged annular channel containing and holding a flexible insert; the flexible insert comprising an inner contact member surrounded by an outer contact member; and forming a flexible annular zone for maintaining a reduced pressure when engaged with a surface of the eye;

d. the upper and lower sections of the body defining an opening through the device;

e. the device having a major and a minor axis, wherein when in use the major axis corresponds to a nasal temporal axis; wherein the distal end of the device defines a shape of a non-planar ellipse; wherein the inner contact member defines an elliptical opening having a major and a minor axis; whereby the elliptical opening is an ellipse; and, f. wherein the major axis of the opening at a distal end of the inner contact member is from about 1.01 to about 1.25 times larger than the minor axis.

21. The device of claim 20, wherein the major axis of the opening at the distal end of the device is from about 1.15 to about 1.2 times larger than the minor axis.

22. The device of claim 20, wherein the major axis of the opening at the distal end of the device is from about 1.1 to about 1.2 times larger than the minor axis.

23. The device of claim 20, wherein the major axis of the opening at the distal end of the device is from about 1.16 to about 1.19 times larger than the minor axis.

24. The device of claim 20, wherein the distal end of the inner contact member is shorter at the minor axis and taller at the major axis.

25. The device of claim 20, wherein the distal end of the outer contact member is shorter at the minor axis and taller at the major axis.

26. The device of claim 20, wherein the inner contact member defines a contact member angle of greater than 90°.

27. The device of claim 20, wherein the outer contact member defines a contact member angle of less than 90°.

28. The device of claim 20, comprising a window over the opening.

29. The device of claim 28, wherein the window is a curved window.

30. The device of claim 29, wherein the window is a contact lens.

31. The device of claim 29, wherein the curved window is configured for contact on the surface of the eye and configured to change the shape of the eye.

32. The device of claim 20, comprising a planar applanation window.

33. The device of claim 20, wherein the inner contact member is configured so that when in use the inner contact member contacts a sclera of the eye, and does not contact a limbus of the eye along the major axis.

34. The device of claim 20, wherein the inner contact member is configured so that when in use the inner member contacts the limbus at the minor axis.

35. The device of claim 20, wherein the opening is larger than a typical human iris, and thereby the device does not obstruct the iris.

\* \* \* \* \*